US008273956B2

(12) United States Patent
Paul et al.

(10) Patent No.: US 8,273,956 B2
(45) Date of Patent: Sep. 25, 2012

(54) METHOD FOR PERFORMING HOMOLOGOUS RECOMBINATION IN PLANTS

(75) Inventors: Wyatt Paul, Pont du Chateau (FR); Sophie Wehrkamp-Richter, Clermont-Ferrand (FR); Jean-Baptiste Laffaire, Mozac (FR)

(73) Assignee: Biogemma S.A.S., Paris (FR)

( * ) Notice: Subject to any disclaimer, the term of this patent is extended or adjusted under 35 U.S.C. 154(b) by 761 days.

(21) Appl. No.: 12/301,358

(22) PCT Filed: May 15, 2007

(86) PCT No.: PCT/EP2007/054693
§ 371 (c)(1),
(2), (4) Date: Dec. 24, 2008

(87) PCT Pub. No.: WO2007/135022
PCT Pub. Date: Nov. 29, 2007

(65) Prior Publication Data
US 2009/0293155 A1 Nov. 26, 2009

(30) Foreign Application Priority Data
May 18, 2006 (EP) .................................... 06114137

(51) Int. Cl.
*A01H 5/00* (2006.01)
*C12N 15/82* (2006.01)
*C12N 15/00* (2006.01)
*C07H 21/04* (2006.01)
(52) U.S. Cl. ..................... 800/298; 800/278; 435/320.1; 536/23.2
(58) Field of Classification Search .................. None
See application file for complete search history.

(56) References Cited

U.S. PATENT DOCUMENTS

| 6,476,297 B1 | 11/2002 | Mascarehas et al. |
| 6,699,686 B1 | 3/2004 | Brocard et al. |
| 2005/1017236 | 8/2005 | Puchta et al. |

FOREIGN PATENT DOCUMENTS

| WO | WO-96/14408 A2 | 5/1996 |
| WO | WO-97/31108 A1 | 8/1997 |
| WO | WO-03/004659 | 1/2003 |
| WO | WO 2005/049842 * | 6/2005 |
| WO | WO-2005/049842 A2 | 6/2005 |

OTHER PUBLICATIONS

Schena et al., A steroid-inducible gene expression system for plant cells, 1991, PNAS 88:10421-10425.*
Aoyama and Chua, A glucocorticoid-mediated transcriptional induction system in transgenic plants, 1997, Plant Journal 11:605-612.*
Brocard et al., A chimeric Cre recombinase inducible by synthetic but not natural ligands of the glucicorticoid receptor. 1998, Nucleic Acids Research 26:4086-4090.*

Brocard, J., et al., "a Chimeric cre recombinase inducible by synthetic, but not by natural ligands of the glucocorticoid receptor," Nucleic Acids Research, 1998, Vo. 26, No. 17, pp. 4086-4090.
Durai, S., et al., "Zinc finger nucleases: custom-designed molecular scissors for genome engineering of plant and mammalian cells," Nucleic Acids Research, 2005, vol. 33, No. 18, pp. 5978-5990.
Chandrasegaran, S. and Smith, J., "Chimeric restoration enzymes: what is next?," Biol. Chem., 1999, vol. 380, pp. 841-848.
Joubes, J., et al., "Conditional, recombinase-mediated expression of genes in plant cell cultures," The Plant Journal, 2004, vol. 37, pp. 889-896.
Aggarwal, A. and Wah, D.A., "Novel site-specific DNA endonucleases," Current Opinion in Structural Biology, 1998, vol. 18, pp. 19-25.
Wright, D.A., et al., "High-frequency homologous recombination in plants mediated by zinc-finger nucleases," The Plant Journal, 2005, vol. 44, pp. 693-705.
Aoyama, T. and Chua, N.-H., "A glucocorticoid-mediated transcriptional induction system in transgenic plants," The Plant Journal, 1997, vol. 11, No. 3, pp. 605-612.
Bleuyard, J.-Y. and White, C. I., "The arabidopsis homologue of Xrcc3 plays an essential role in meiosis," The EMBO Journal, 2004, vol. 23, pp. 439-449.
Choulika, A., et al., "The yeast I-Sce I meganuclease induces site-directed chromosomal recombination in mammalian cells," Life Sciences, 1994, vol. 317, pp. 1013-1019.
Choulika, A., et al., "Induction of homologous recombination in mammalian chromosomes by using the I-Scel system of *Saccharomyces cerevisiae*," Molecular and Cellular Biology, 1995, vol. 15, No. 4, pp. 1968-1973.
Dingwall, C. and Laskey, R.A., "Protein import into the cell nucleus," Ann. Rev. Cell. Biol., 1986, vol. 2, pp. 367-390.
Doutriaux, M.-P., et al., "Isolation and characterisation of the RAD51 and DMC1 homologs from *Arabidopsis thaliana*," Mol. Gen. Genet., 1998, vol. 257, pp. 283-291.
Jacquier, A. and Dujon, B., "An intron-encoded protein is active in a gene conversion process that spreads an intron into a mitochondrial gene," Cell, 1985, vol. 41, pp. 383-394.
Kalderon, D., et al., "Sequence requirements for nuclear location of simian virus 40 large-T antigen," Nature, 1984, vol. 311, pp. 33-38.
Kathiresan, A. and Khush, G.S., "Two rice DMC1 genes are differentially expressed during meiosis and during haploid and diploid mitosis," Sex Plant Reprod., 2002, vol. 14, pp. 257-267.
Klimyuk, V.I. and Jones, J.D.G., "AtDMC1, the *Arabidopsis* homologue of the yeast DMC1 gene: characterization, transposon-induced allelic variation and meiosis-associated expression," The Plant Journal, 1997, vol. 11, No. 1, pp. 1-14.
Lanford, R.E. and Butel, J.S., "Construction and characterization of an SV40 mutant defective in nuclear transport of T antigen," Cell, 1984, vol. 37, pp. 801-813.

(Continued)

*Primary Examiner* — Elizabeth McElwain
(74) *Attorney, Agent, or Firm* — Connolly Bove Lodge & Hutz LLP

(57) ABSTRACT

The invention relates to modified restriction enzymes capable of being used for promoting homologous recombination in organisms, in particular plants, making it possible to either target gene integration or excise unwanted DNA sequences in the genome of said organisms.

10 Claims, 9 Drawing Sheets

OTHER PUBLICATIONS

Figure 1:
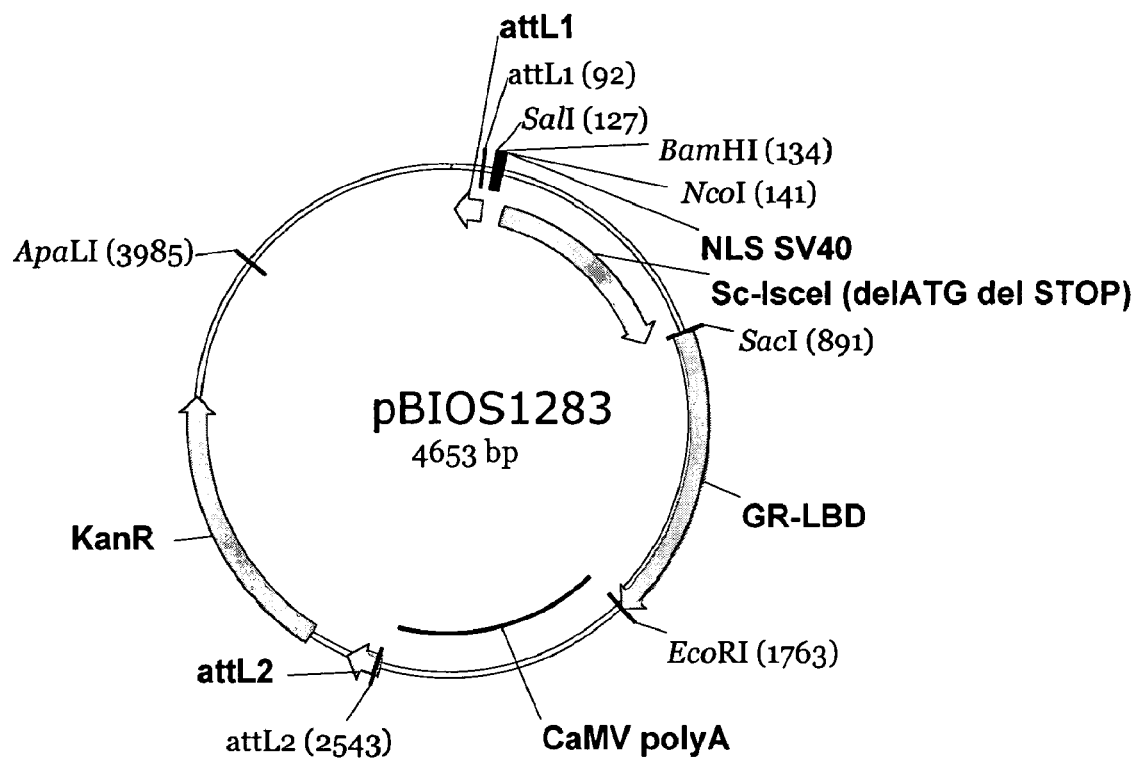

Mader, S. and White, J.H., "A steroid-inducible promoter for the controlled overexpression of cloned genes in eukaryotic cells," Proc. Natl. Acad. Sci., 1993, vol. 90, pp. 5603-5607.

Marshall, P. and Lemieux, C., "Cleavage pattern of the homing endonuclease coded by the fifth intron in the chloroplast large submit rRNA-encoding gene of *Chlamydomonas eugametos*," Gene, 1991, vol. 104, pp. 241-245.

Miesfeld, R., et al., "Genetic complementation of a glucocorticoid receptor deficiency by expression of cloned receptor cDNA," Cell, 1986, vol. 46, pp. 389-399.

Monnat, Jr., et al., "Generation of highly site-specific DNA double-strand breaks in human cells by the homing endonucleases I-Ppol and I-Crel," Biochemical and Biophysical Res. Communications, 1999, vol. 255, pp. 88-93.

Morita, R., "Assessment of utility of meiosis-associated promoters of lily for induction of germinal Ds transposition in transgenic rice," Plant Cell Physiol., 2003, vol. 44, No. 6, pp. 637-642.

Plessis, A., et al., "Site-specific recombination determined by I-Scel, a mitochondrial group I intron-encoded endonuclease expressed in the yeast nucleus," Genetics, 1992, vol. 130, pp. 451-460.

Pruneda-Paz, J.L., et al., "Identification of a novel steroid inducible gene associated with βhsd locus of *Comamonas testosteroni*," J. of Steroid Biochemistry & Molecular Biology, 2004, vol. 88, pp. 91-100.

Schena, M., et al., "A steroid-inducible gene expression system for plant cells," Proc. Natl. Acad. Sci., 1991, vol. 88, pp. 10421-10425.

Silva, G.H., et al., "Crystal structure of the thermostable archaeal intron-encoded endonuclease I-Dmol," J. Mol. Biol., 1999, vol. 286, pp. 1123-1136.

Wang, J. et al., "Purification, biochemical characterization and protein-DNA interactions of the I-Crel endonuclease produced in *Escherichia coli*.," Nucleic Acids Research, 1997, vol. 25, No. 19, 3767-3776.

White, J.H., "Modified steroid receptors and steroid-inducible promoters as genetic switches for gene therapy.," Advances in Pharmacology, 1997, vol. 40, pp. 239-267.

* cited by examiner

METHOD FOR PERFORMING HOMOLOGOUS RECOMBINATION IN PLANTS

RELATED APPLICATIONS

This application is a national stage application (under 35 U.S.C. 371) of PCT/EP2007/054693 filed May 15, 2007, which claims benefit of European application 06114137.0 filed May 18, 2006.

The invention relates to modified restriction enzymes capable of being used for promoting homologous recombination in organisms (mammals and plants), in particular plants, making it possible to either target gene integration or excise unwanted DNA sequences in the genome of said organisms.

Homologous recombination (HR) is useful for specifically inserting sequences at a given target site in a genome. It can also be used to perform allele replacement. This can be used for curing genetic disease in humans, for example, or for plant improvement.

Furthermore, it is possible to use homologous recombination for nuclear genomic DNA excision, which allows the removal of undesirable exogenous DNA sequences. As an example, in plants, this can be used for removing the selectable marker used in plant transformation, or for the irreversible controlled activation or inactivation of transgenes.

Homologous recombination when integrating a DNA sequence in a genome also solves the problem residing in the random pattern of integration of the heterologous gene into said genome. Indeed, it is known that such random integration may lead to a wide variation in the level of expression of the genes among different transformed organisms after regeneration, thus increasing the cost and lengthening the selection of interesting transformants. Furthermore, it is always possible that these heterologous genes are integrated within endogenous genes, thus disrupting their expression. This is a real problem when these endogenous genes are necessary for the maturation, differentiation and/or viability of the cells or organism.

Gene targeting uses the selection of integration events obtained by homologous recombination between DNA sequences present in the genome of a cell or organism and introduced heterologous DNA sequences. This provides a possibility of controlling the site of integration of these heterologous DNA sequences.

Homologous recombination is nevertheless difficult to achieve as mammalian and plant cells have also a greater propensity to mediate non-homologous recombination. This is in particular true for plant cells.

This bad ability to mediate homologous recombination events is also problematic when the transformed organism is difficult to transform, in particular when the in vitro culture or regeneration steps of the cells is difficult. As an example, even though it is now widely possible to transform maize, the rate of transformation is still quite poor and necessitates to perform multiple transformation experiments to obtain an adequate number of transformed plants (transformation rate of about 4%). As the homologous recombination rate in regular maize plants is very low, one can thus conceive that it is very difficult and time consuming to select transformed maize where HR occurred if the system is not improved.

Thus, there is a need for developing gene targeting systems allowing the possibility to routinely obtain and select homologous recombinants at a high enough frequency with the selection and screening protocols.

As indicated above, homologous recombination can be used for inserting new heterologous sequences, but also for eliminating, removing or substituting sequences (creating new alleles) within the organism genome.

Replacement by homologous recombination of a wild type gene on a chromosome (the target gene) by either a target gene with a new expression cassette, an inactivated gene or a modified gene (new allele) is hampered by the high frequency of random insertion of the whole vector (non-homologous recombination) in animal cells, rather than gene replacement (homologous recombination).

It is possible to use positive/negative selection markers for counter-selection of random insertion events. For example, the thymidine kinase (TK) gene from herpes simplex virus may be used as the negative selection marker. Nevertheless, the vectors are sometimes unstable, and need multiple cloning steps to be made, increasing the time needed to produce them.

Thus, there remains a need for developing new systems for gene targeting by homologous recombination in various organisms and in particular in plants.

It has been reported that creation of a double strand break (DSB) or breaks in the vicinity of the site in which homologous recombination is wished will increase the frequency of HR. These DSB may be created by the use of a restriction enzyme, or a meganuclease, which is a specific restriction enzyme that recognizes and cut DNA at long (more than 15 bp) sites.

The inventors also postulate that the efficiency of homologous recombination may increase depending on the state of the cell. In particular, it is postulated that the efficiency will be better when the cell is at the meiosis stage.

It is therefore desirable to provide a system that will improve the frequency of homologous recombination, through a control of the double-strand breaks in the genome of the target host.

It is to be noted that homologous recombination can also be used as a tool for removing exogenous DNA sequences that do not contribute to the new phenotype conferred by the transgene, such as selectable marker genes that are necessary for plant transformation and particularly those marker genes that confer herbicide or antibiotic resistance.

It can be performed by the use of a restriction enzyme or a meganuclease to create a double strand break (DSB) or breaks in the vicinity of duplicated (homologous) DNA. Such DSBs increase the frequency of HR and intervening DNA excision in the target organism thus allowing precise and efficient DNA excision. Additionally the creation of DSBs flanking the DNA to be excised allows DNA excision via NHEJ.

For this purpose, it is also important to have a good percentage of excision for it to be useful from an industrial point of view, and in particular to have a high level of T1 plants in which excision of the marker gene has occurred. Use of the controllable/inducible enzyme of the invention responds to this question.

Systems for excision of DNA sequences by producing a transgenic line containing a target vector and crossing this line to an I-SceI expressing line to excise the DNA fragment are also proposed, as well as the construction of a target vector containing the sequence coding for an inducible I-SceI sequence on the DNA fragment to be excised. Both methods allow excision of the DNA fragment in a protocol with few steps.

In a first embodiment, the present invention relates to an isolated nucleic acid comprising a nucleic acid coding for a restriction enzyme capable of cutting a DNA sequence at a predetermined site, fused with a nucleic acid coding for a rat Glucocorticoid Receptor (GR) Ligand Binding Domain (LBD) (Miesfeld et al. 1986) depicted in SEQ ID No. 1 (protein) coded by SEQ ID No. 2 (nucleic acid).

In a preferred embodiment, the GR LBD sequence used in the invention contains a first NLS (nuclear Localization Signal, NL1) in the LBD sequence and a second incomplete NLS (NL2) upstream of the LBD sequence. Indeed, although such a restriction enzyme GR-LDB fusion can be imported into the nucleus on hormone binding, more efficient nuclear importation in the presence of the hormone can be assured by adding a further nuclear Localization Signal (NLS) to the fusion. A preferred NLS is the SV40 Large T antigen NLS (Dingwall et al. 1986, Lanford and Butel 1984, Kalderson et al. 1984) depicted in SEQ ID No. 3 (protein) coded by sequence ID No. 4 (nucleic acid) but other NLS sequences can be used.

Any restriction enzyme may be used for the purpose of the invention. In particular, one can use EcoRI, EcoRV, BamHI, HindIII, or any enzyme described in the literature or on internet sites such as http://rebase.neb.com/rebase/rebase.html. All these enzymes are well known to the person skilled in the art, and their sequences and origin can easily be found in the literature or on internet sits such as the NCBI site at http://www.ncbi.nlm.nih.gov. These enzymes are also named sequence specific endonucleases.

Obtaining a fused protein is performed by classical molecular biology methods as described in Sambrook. As an example, one can amplify the DNA sequence coding for the restriction enzyme, using a set of primers, one of them comprising a linker sequence, then amplify the DNA sequence coding for the rat glucocorticoid receptor with an appropriate set of primers, one of them also comprising a linker sequence, and perform the fusion by ligation between the two linker sequences.

For the purpose of the invention, it is nevertheless preferable that the restriction enzyme does not have many cutting sites in the genome of the host. Thus in a preferred embodiment, the restriction enzyme of the invention recognizes and cuts a site that is at least 15 bases, and preferably at least 18 bases. Indeed, it is statistically demonstrated that the longer the restriction site, the less chance it is present in a genome. In this case, the restriction enzyme is called a meganucleases, which is by definition a sequence-specific endonuclease with large (>12 bp) recognition sites.

In the context of the present invention, said meganuclease is preferably I-SceI, described as SEQ ID No. 5 (protein) and 6 (nucleic acid). Nevertheless, other meganucleases may also be used, such as HO, or the meganuclease described in Epinat et al (Nucleic Acids Research, 2003, Vol. 31, No. 11 2952-2962), in particular the hybrid meganuclease, in Chames et al (Nucleic Acids Res., Nov. 23, 2005; 33(20): e178-e178), or in Nomura et al (I-Apel, Nucleic Acids Res., Jul. 26, 2005; 33(13): e116-e116.), or in Silva et al (I-DmoI, Nucleic Acids Res., Jun. 9, 2004; 32(10): 3156-3168).

One can also cite I-CreI (Wang et al (1997) Nucleic Acids Res., 25, 3767-3776) or I-CeuI (Marshall et al (1994) Eur. J. Biochem., 220, 855-859), which function as homodimers, or larger proteins bearing two (do)decapeptide motifs, such as I-SceI (Jacquier et al (1985) Cell, 41, 383-394), PI-SceI (Gimble, et al (1996) J. Mol. Biol., 263, 163-180) and I-DmoI (Dalgaard et al. (1993) Proc. Natl Acad. Sci. USA, 90, 5414-5417).

The construct of the invention can be made with any restriction enzyme or meganuclease that is currently known, once its sequence has been isolated, as it is obtained through completely classical methods of molecular biology.

In the preferred embodiment of the invention, the isolated nucleic acid of the invention is such that said nucleic acid coding for a rat glucocorticoid receptor is fused at the 3' end of said nucleic acid coding for a restriction enzyme. The person skilled in the art understands that in another embodiment, said nucleic acid coding for a rat glucocorticoid receptor is fused at the 5' end of said nucleic acid coding for a restriction enzyme.

In a preferred embodiment, the isolated nucleic acid of the invention codes for a protein having SEQ ID No. 7. It is preferred that this nucleic acid has SEQ ID No. 8.

The invention also relates to an expression cassette comprising a promoter operably linked to the nucleic acid of the invention. Any promoter is suitable, and some are described below.

As indicated above, the restriction enzyme of the invention is useful for improving homologous recombination in organisms such as cells, which can be issued from mammals (rodents such as rats and mice, and human cells included, when performed in vitro), or in whole organisms such as rodents, but also pigs, cattle, cats and dogs. In those cases a mutant GR LBD (Brocard et al., 1998) which binds synthetic ligands such as dexamethasone but not natural GR ligands is most preferably used. The invention can also be performed on whole plants, and the invention also encompasses a transgenic plant transformed with the nucleic acid of the invention. In the embodiments of the invention, said "plant" is a monocotyledon or a dicotyledonous. In preferred embodiments, said plant is a monocotyledon, and is preferably wheat or maize. In the most preferred embodiment, said plant is maize.

The modification to the restriction enzyme implicates that it is not active without an external stimulus (application of dexamethasone), or less active than the non-modified restriction enzyme. Upon application of this hormone, the restriction enzyme enters the nucleus of the cells, and performs the double strand break at its site of recognition. The invention also encompasses a restriction enzyme coded by the nucleic acid of the invention.

The invention also relates to a method for promoting a genomic double strand break at a predetermined restriction site R in the genome of a plant, comprising the steps of transforming said plant with an nucleic acid coding for a restriction enzyme fused with a nucleic acid coding for a rat Glucocorticoid Receptor (GR) Ligand Binding Domain (LBD), wherein said restriction enzyme is capable of cutting at said predetermined restriction site R, and applying dexamethasone to cells of said transformed plant in order to promote genomic double strand break at said predetermined restriction site R.

In another embodiment, the invention also relates to a method for obtaining a plant in the genome of which a specific DNA fragment has been excised, comprising the steps of:
  a. providing a plant comprising, in its genome, a polynucleotide X comprising said DNA fragment, wherein said polynucleotide comprises at least a restriction site R, rare or absent in the genome of said plant, at its 5' or 3' extremity,
  b. providing to cells of said plants the restriction enzyme of the invention, that recognizes and cuts at said restriction site(s) R and applying dexamethasone in order to generate a double strand break(s) at said site(s)

thereby obtaining a plant wherein said DNA fragment has been excised after cutting at said restriction site(s) R and repair of the lesion generated by the double strand break(s).

In preferred embodiments, one or two R sites are used. When two sites are used, they preferably flank the X polynucleotide (i.e. they are located at its 3' and 5' ends).

The DNA fragment to be excised may have been introduced in the plant by transforming said plant with a vector containing said fragment, by methods known in the art, such as *Agrobacterium* transformation.

In a specific embodiment, said polynucleotide X is flanked by two homologous regions Y and Y'.

The Y and Y' sequences are said to be "homologous" if they present at least 90%, more preferably 95% even more preferably 100% identity, over at least 50, more preferably 100 consecutive nucleotides (nt) even more preferably 200 or 500 nt, even more preferably 1000 nt, even more preferably 2000 nt.

"Rare cutting enzyme restriction site "R" means a restriction site of an endonuclease which has a low (<0.1%, more preferably <0.05 or 0.01%) probability to be present in the genome of the target organism. In maize, it is believed that such restriction site is at least 15 nucleotides long, more preferably equal or greater to 18 nucleotides long. As indicated above, as an example of rare cutting enzyme restriction sites, one can cite I-Sce I, from an mobile intron of *Saccharomyces cerevisiae* (Jacquier and Dujon 1985, Plessis et al., 1992), which has a recognition site of 18 bp, as well as other meganucleases such as I-DmoI, I-CreI, I-CeuI, l-PpoI, PI-SceI, (Aggarwal and Wah 1998, Wang et al., 1997, Monnat et al., 1999, Silva et al., 1999, Marshall et al., 1991), this list being non limitative.

The preferred enzyme is I-SceI, having the sequence SEQ ID No. 5. As its cutting site is 18 bp long, this restriction enzyme has a low probability of cutting DNA in plants, and in maize in particular. The I-SceI enzyme has been isolated from *Saccharomyces cerevisiae* and double strand breaks induced by this enzyme increase the rate of homologous recombination in mammalian cells (Choulika et al., 1994, 1995 and WO9614408).

"Double strand break (DSB)", is the lesion on both strands of a double strand DNA, caused by the restriction enzyme at this rare cutting enzyme restriction site R. This DSB induced the formation of "cut-ends".

"The repair of the lesion generated by the DSB" refers to the mechanism by which a re-attachment may occur between the free strands generated by "cut-ends". This re-attachment may occur at the site or next to the site of the "cut-end" but also at a more distal place to the DSB. This may be performed by homologous recombination (HR) or by non-homologous end-joining (NHEJ).

According to an embodiment, said polynucleotide X comprises two restrictions sites R, one being located at its 5' end the other being at the 3' end, and there is no homologous region Y and Y'.

According to another embodiment, said polynucleotide X comprises two restrictions sites R, one being located at its 5' end and the other being at its 3' end, and is flanked by homologous regions Y and Y'.

In yet another embodiment, said polynucleotide X comprises only one restriction site R at its 5' or 3' end and is flanked by homologous regions Y and Y'.

In the present invention, said restriction enzyme may be provided by the expression, within cells of said plant, of a sequence coding for said enzyme. Methods for the expression of proteins from DNA sequences in plants are well known to persons skilled in the art.

For being expressed, a sequence coding for this enzyme may be present in the cell under the control of a constitutive, tissue specific, developmentally regulated, inducible or meiosis promoter. Examples of constitutive promoters useful for expression include the 35S promoter or the 19S promoter (Kay et al., 1987), the rice actine promoter (McElroy et al., 1990), the pCRV promoter (Depigny-This et al., 1992), the CsVMV promoter (Verdaguer et al., 1998), the ubiquitin 1 promoter of maize (Christensen et al., 1996), the regulatory sequences of the T-DNA of *Agrobacterium tumefaciens*, including mannopine synthase, nopaline synthase, octopine synthase.

Promoters may come from the same species or from another species (heterologous promoters). Although some promoters may have the same pattern of regulation when there are used in different species, it is often preferable to use monocotyledonous promoters in monocotyledons and dicotyledonous promoters in dicotyledonous plants.

"Meiosis promoter" means a promoter which may allow the transcription of the operably linked sequence within cells undergoing "meiosis". Examples of meiosis promoter are the promoter Lim10 from *Lilium longifolium* (Morita et al., 2003, see SEQ ID No. 13), AtXrcc3 (Bleuyard and White 2004), AtCDC45 (Stevens et al., 2004), AtDMC1 from *Arabidopsis thaliana* or OsDMC1 from *Oriza sativa*, (Klimyuk and Jones, 1997; Doutriaux et al., 1998; Kathiresan et al., 2002), AtMEI1 (U.S. Pat. No. 6,476,297). Such a meiosis promoter should be ideally meiosis-specific or preferentially active during meiosis.

According to another embodiment, expression of said restriction enzyme may be inducible.

By "inducible", it is meant that the enzyme only becomes active in response to an external stimulus. This stimulus may be a chemical or mechanical stimulus.

In a preferred embodiment, the sequence encoding said restriction enzyme is under the control of an inducible promoter. As an illustration, the inducible promoter may be induced by a stress or a chemical agent.

Inducible promoters may be induced by pathogens or wounding, more preferably they are induced by abiotical stress like cold, heat, UV light, high salt and water deficit. Promoters useful for targeted expression in trangenesis are reviewed in Potenza et al., 2004. Some abiotic stress promoters are the *Arabidospsis thaliana* or *Oriza sativa* DREB genes promoters (Dubouzet et al., 2003; Lee et al., 2004; Pellegrineschi et al., 2004); the *Oriza sativa* SISAP1, CDPK7 or WSI gene promoters (Mukhopadhyay et al., 2004; Saijo et al., 2000; Takahashi et al., 1994) the *A. thaliana* rd29 gene promoters (Yamaguchi-Shinozaki and Shinozaki 1993). Some plant heat inducible promoters may also be used hsp18.2 or hsp101 from *A. thaliana* (Yoshida et al., 1995; Young et al., 2005), hsp17.6 or hsp17.3 from Glycine max (Severin and Schoffl, 1990; Saidi et al., 2005). DNA microarrays have been used to identify stress regulated sequences (Rabbani et al., 2003; EP 1 452 596; WO 02/16655) The signalisation pathway of the response to stress includes abscisic acid signalisation so ABA-inducible promoters may also be powerful stress-inducible promoters, such as the *Horgum vulgare* A22 and hva1 promoters (Shen et al., 1993; Straub et al., 1994), Zea maize rab 17, DBF1 and DBF2 (Villardel et al., 1990; Kizis and Pages, 2002), *Arabidopsis thaliana* ABF3 (Genbank accession AK175851), and *Oriza sativa* rab21 (Mundy and Chua, 1988).

In another embodiment, the foreseen promoters are induced by chemicals (for review, see Moore et al., 2006, Padidam M. 2003 and Wang et al., 2003 and Zuo and Chua 2000). Some examples of couples of chemically inducible systems and chemical inducer used in plants are, the alcA promoter from *A. nidulans*, inducible by the Ethanol (Roslan et al., 2001) or the ecdysone receptor from *C. fumiferana*, inducible by an ecdysone agonist (Koo et al., 2004).

In another embodiment, expression of the enzyme is indirectly induced by a chemical. As an illustration, one can use the GVG gene, which codes for a modified rat glucocorticoid responsive transcription factor that remains in the plant cytosol as a complex. On dexamethasone application, this complex dissociates such that the GVG protein enters the nucleus and binds to the target DNA sequences (UAS). Transcription from the UAS promoter allows the production of the modified I-SceI. This is considered as a dexamethasone inducible (although indirectly) promoter used to control the restriction enzyme expression (Aoyama and Chua (1997). In this case, application of dexamethosone will induce both the restriction enzyme expression and its activity.

Said restriction enzyme may also be provided by crossing a transgenic line containing said polynucleotide X, with another transgenic line containing a sequence coding for said enzyme. As previously described, this sequence may be present in this transgenic line under the control of a constitutive, developmentally regulated or inducible promoter.

It is also foreseen to provide said restriction enzyme by a transient expression system, such as agro-infiltration or by any other way, such as injection or spray.

According to a preferred embodiment, the restriction enzyme will have a peak of activity during meiosis. "Meiosis" is the specific cell division leading to gametes production, and the inventors believe that meiosis is a preferred phase for recombination in plants, even though recombination may also occur during mitosis.

In an embodiment, dexamethasone is applied during meiosis, or just before meiosis.

In another embodiment, the sequence encoding said restriction enzyme is under the control of a meiosis promoter. In this case, dexamethasone may be applied also during meiosis or can be available at any development stage.

Dexamethasone can be applied to the cells of the plant in several ways. As a solution it can be sprayed on to leaves (Aoyama et al., 1997) or floral organs, applied in drops to the plant surface, for example onto the whorls, added as a drench in watering, it can be injected into the vasculature or infiltrated under vacuum. Seeds can be imbibed in a dexamethosone solution. Additionally dexamethosone induction can be achieved in vitro by growing seedlings on media containing dexamethasone. For induction just prior to meiosis the techniques of root drenching, injection of the vasculature below the floral meristem, spraying or infiltration of buds or applying drops to the floral meristem are preferred.

In an embodiment of the above-described method, the purpose is to eliminate a specific DNA fragment in the vicinity of a restriction site recognized by a restriction enzyme according to the invention. A DSB is performed and the reattachment/repair of this DSB leads to excision of this specific DNA fragment.

In a preferred way of realization of the invention, the attachment of said DSB is performed by homologous recombination (HR) between said homologous Y and Y' sequences, and leads to the excision of the DNA fragment and one copy of the recombinated Y or Y' sequence.

For HR recombination, strong sequence homology (more than about 90% identity) needs to be present between the two sequences Y and Y', and preferably identity.

It is also to be noted that the enzyme of the invention can be used in another way of realization of the invention, where said attachment of said cut ends (repair of DSB) is performed by non homologous end joining (NHEJ) and at least part of the sequences flanking said DSB-generated fragments are attached together.

Non homologous end joining is also known as "illegitimate recombination", this method results from the attachment of the two DNA strands produced by the DSB "double strand break", no homologous region are necessary for this method but homologous regions may be present on each DNA strand. The attachment of these strands may result to the reconstitution of the restriction enzyme recognition site.

In specific embodiments of the present invention said DNA fragment X to be eliminated comprises a chimeric gene consisting of a promoter linked to a selectable marker gene and a polyadenylation sequence, the selectable marker gene giving resistance to an antibiotic or an herbicide to said plant. More preferably the selectable marker gene comprises of a gene in the group consisting of the pat, the bar or the nptII genes. In the present invention, the term "selectable marker", "selectable gene", "selectable marker gene", "selection marker gene", "marker gene" are used interchangeably. These selectable markers include, but are not limited to, antibiotic resistance genes, herbicide resistance genes or visible marker genes.

Other phenotypic markers are known in the art and may be used in this invention. A number of selective agents and resistance genes are known in the art. (See, for example, Hauptmann et al., 1988; Dekeyser et al., 1988; Eichholtz et al., 1987; and Meijer et al., 1991). Notably the selectable marker used can be the bar or pat genes conferring resistance to bialaphos (White et al., 1990), the sulfonamide herbicide Asulam resistance gene, sul (described in WO 98/49316) encoding a type I dihydropterate synthase (DHPS), the nptII gene conferring resistance to a group of antibiotics including kanamycin, G418, paromomycin and neomycin (Bevan et al., 1983), the hph gene conferring resistance to hygromycin (Gritz et al., 1983), the EPSPS gene conferring tolerance to glyphosate (U.S. Pat. No. 5,188,642), the HPPD gene conferring resistance to isoxazoles (WO 96/38567), the gene encoding for the GUS enzyme, the green fluorescent protein (GFP), expression of which, confers a recognisible physical characteristic to transformed cells, the chloramphenicol transferase gene, expression of which, detoxifies chloramphenicol. Advantageously, the selectable marker gene is inserted between a promoter and a terminator.

According to this advantageous embodiment, the marker gene is preferably controlled by a promoter which allows expression in cells, thus allowing selection of cells or tissue containing the marker at any stage of development of the plant. Preferred promoters are the promoter of nopaline synthase gene of *Agrobacterium*, the promoter derived from the gene which encodes the 35S subunit of cauliflower mosaic virus (CaMV) coat protein, and the rice actin promoter. However, any other suitable second promoter may be used. Any terminator may be used. Other elements like introns and enhancers can also be present in the nucleic sequence of interest in order to improve the expression of the gene of interest. One could in particular note the FAD2 intron from *Arabidopsis* described in WO 2006/003186.

In this specific embodiment one can obtain a transformed plant by the use of the marker gene selection and, in a further step remove the marker gene by the protocol of the invention, the marker gene being located on the fragment X. In this particular protocol the restriction enzyme activity which is dependant of application of dexamethasone may be further controlled, for example through use of a meiotic promoter, or of a dexamethasone inducible promoter.

In one of the embodiment of this invention, the sequences encoding the restriction enzyme are located within said fragment to be excised.

In this embodiment, it may also be useful for the sequence encoding the restriction enzyme to be under the control of an inducible or a tissue or developmentally regulated promoter.

It is to be noted that, in another embodiment, excision of the DNA fragment, in particular by homologous recombination can lead to production of an expressible polynucleotide.

The method of the invention thus makes it possible to have conditional expression of a given gene, especially when the restriction enzyme is under the control of an inducible promoter and is located within the DNA fragment to be excised.

In this embodiment, the expression cassette used in this invention, may contain from 5' to 3': a promoter, a first polynucleotide Y1, a polynucleotide Y, said sequence X to be excised, flanked in 5' or 3' or both by said restriction site R, said polynucleotide Y, a second polynucleotide Y2, and a terminator sequence. In this embodiment, the polynucleotide Y1YY2 formed after removal of sequence X by homologous recombination makes a complete coding sequence imparting a desired phenotype in said plant.

For irreversible control activation of a protein, the fragment to be excised is inserted in the sequence encoding for a protein in such a way, that the interrupted sequence will not lead to a correctly transcribed RNA and a functional protein. The insertion may be done in the coding sequence but also in an intron or in the promoter. In this embodiment, the excision of the given fragment allows the correct expression of the protein.

The plant containing this construct may be re-transformed or crossed with a transgenic line containing the sequence encoding the restriction enzyme of the invention. Excision of the fragment may be observed in the lineage of the plant containing both constructs. Induction of the restriction enzyme activity by dexamethasone in the plant containing both constructs allows the precise production of the given protein. For this embodiment, one useful stimuli may be high or cold temperature. In such a mode of realization the invention offers a new binary system for control expression of protein. Such system may be of interest for example for the production of recombinant proteins of therapeutics usage.

For this particular usage, the restriction enzyme coding gene may also be under the control of a tissue specific promoter to induce the expression of a recombinant protein in this related tissue. Examples of tissue specific promoters may be root specific, such as the rcc2 or rcc3 promoters (Xu et al., 95), seed specific such as the HMWG (Norre et al., 2002) and Zein promoters (Russell and Fromm 97) or leaf specific such as the rubisco (Bansal et al., 92) or PEPC promoters (Matsuoka et al., 1994).

The invention relates to the excision of a DNA fragment from the genome of a plant. If this fragment contains a sequence coding for a protein, the excision may lead to the inactivation of this coding sequence.

As previously indicated, the described methods may be used in any organisms, such as mammals or plants, or cells of mammals or plants. It is particularly useful on dicotyledonous and monocotyledonous plants, preferably for monocotyledonous, including but not limited to maize, wheat, barley, rice, rye, oat, triticale. Tomato, pepper, lettuce, beet, carrots, melon, rape, sunflower are also plants (list non limitative) in which the method of the invention may be performed. Preferably said plant is maize. The invention also encompasses transformed plants containing the elements described above, or being obtained by methods of the invention. The invention also encompasses cells of plants containing the elements described above, or being obtained by methods of the invention.

The transgenic plant containing the sequence encoding the restriction enzyme may also be crossed with another plant containing the expression cassette of the invention containing a polynucleotide X comprising the DNA fragment to be excised according to the invention, said polynucleotide comprises at least a R restriction site rare or absent in the genome at its 5' or 3' extremity or with X. In the obtained plants containing both constructs, the excision of the fragment and selection of the plant with the excised fragment, may be done as previously described for the re transformed plant.

Plant with an excised DNA fragment can be identified by any mean known by a person skilled in the art. Such means include PCR, Southern, Northern or Western hybridisations designed to detect the loss of the excised fragment.

If the excised fragment contains a sequence encoding a selectable marker the absence of this marker may be the way for identification of these plants. "Negative markers" may also be used for this selection. A "negative marker" is a marker the presence of which is deleterious to the plant generally in the presence of an inducer, so that the selection of the plant on said inducer (selective agent) allows the selection of plants in which the excision has occurred and said negative marker has been deleted. Example of "negative markers" are reviewed in Miki and McHugh (2004), as cytosine deaminase (Babwah et al., 2000; Iida and Terada 2005), or diphtheria toxin A (Terada et al., 2004). An other negative marker is D-amino acid oxidase (Erikson et al., 2004). These negative markers may be under the control of an inducible promoter to allow the development of plants before the excision step. In this particular way of achieving the invention, one can transform a plant with the given construct containing the sequence encoding for the negative marker under the control of an inducible promoter. The plant may be retransformed or crossed with a plant containing a sequence encoding the restriction enzyme, or infiltrated by this enzyme. The expression of the given enzyme allows the excision of the DNA fragment according to the invention. Selection on a specific selective agent selects against plants that still contain the negative selection marker and allows the selection of the plants where the excision has occurred.

Plants in which an excision by HR according to the invention occurs may also be selected by the use of traditionally used selection markers. For this specific embodiment, the construct used may contain in the following order (from 5' to 3') a promoter, a first polynucleotide Y1, a polynucleotide Y, the sequence X to be excised flanked in 5', 3' or both by a restriction site R, a second polynucleotide Y, a polynucleotide Y2 and a terminator sequence. In this example the polynucleotide Y1YY2 obtained after excision of the DNA fragment encodes for a selection marker. The use of this selection marker allows the selection of plants where the fragment excision occurs. Examples of such markers have been described above, such as gene coding for resistance to herbicide.

Transgenic lines containing the polynucleotide X or expressing the restriction enzyme of the invention are obtained by traditional methods for genetic transformation of plants and can be obtained by any one of the techniques known to one skilled in the art: methods of direct transfer of genes such as direct micro-injection into plant embryoids (Neuhaus et al., 1997), vacuum infiltration (Bechtold et al. 1993) or electroporation (Chupeau et al., 1989) or the bombardment by gun of particles covered with the plasmidic DNA of interest (Fromm et al., 1990, Finer et al., 1992). Agrobacterium mediated transformation methods may also be used *Agrobacterium tumefaciens*, in particular according to the method described in the article by An et al., (1986), or *Agrobacterium rhizogenes*, in particular according to the method described in the article by Guerche et al., (1987). According to a preferred mode, it is possible to use the method described by Ishida et al., (1996) for the transformation of maize.

In another embodiment, the invention relates to methods of gene targeting and insertion of genes within the genome of an organism, in particular a plant, using the improvement of homologous recombination through the double strand breaks induced by the enzymes according to the invention.

The invention relates in particular to a method for integrating a DNA sequence Z at a predetermined location within the genome of a plant comprising the steps of:
a. providing a plant comprising, at said determined location in its genome, a restriction site R, that is preferably rare or normally absent in the genome of said plant, wherein said site is flanked by a sequence Y3' and a sequence Y5' respectively at its 3' and 5' ends,
b. providing to cells of said plant a nucleic acid comprising said DNA sequence Z flanked by sequences homologous or identical to Y3' and Y5', respectively at its 3' and 5' ends,
c. providing to said cells said restriction enzyme of the invention, and applying dexamethasone in order to induce a double strand break at said restriction site R,
thereby leading to integration of said DNA sequence Z within the plant genome by homologous recombination between said Y3' and Y5' sequences present in the genome of the plant, and said sequences homologous or identical to Y3' and Y5' flanking said sequence Z.

As for the method of excision of a DNA fragment that is described above, the restriction enzyme is provided either by transformation of the receiving host by a nucleic acid of the invention, or by crossing the receiving host with a host which comprises a nucleic acid of the invention in its genome. Transient expression systems are also foreseen.

It is also clear that this method is also applicable to cell cultures or to other organisms such as mammals, as described above. In particular, the method is applicable to mammalian cells, such as human or rodent cells.

The method thus comprises the steps of
a. providing a cell comprising, at a determined location in its genome, a restriction site R, that is preferably rare or normally absent in the genome of said cell, wherein said site is flanked by a sequence Y3' and a sequence Y5' respectively at its 3' and 5' ends,
b. providing to said cell a nucleic acid comprising said DNA sequence Z flanked by sequences homologous or identical to Y3' and Y5', respectively at its 3' and 5' ends,
c. providing to said cell said restriction enzyme of the invention, and applying dexamethasone in order to induce a double strand break at said restriction site R,
thereby leading to integration of said DNA sequence Z within the cell genome by homologous recombination between said Y3' and Y5' sequences present in the genome of the cell, and said sequences homologous or identical to Y3' and Y5' flanking said sequence Z.

The restriction enzyme is added to the cell through transformation, by electroporation, transfection, or any other method known in the art.

The promoters, marker, genes and any other elements for use in this embodiment have been described above.

It is preferred when the sequence Z to be inserted is flanked by Y3' and Y5' sequences identical to the sequences already present in the genome of the receiving host. Preferred size and identity percentages of these sequences have been described above.

As described above, when applying this method to a whole organism and in particular a plant, it is preferred that the restriction enzyme of the invention is made active during meiosis. This may be obtained by application of dexamethasone during meiosis or by use of meiosis-specific or inducible promoters as described above, and permanent application of dexamethasone, as described above.

Screening of organisms which harbour integration of the cassette by homologous recombination within the genome is performed by method known to persons skilled in the art, such as PCR, Southern blots, or any other method. It is also possible to use counter-selectable markers to select these organisms, although this is not the preferred embodiment of the invention.

When the restriction site R is normally absent from the genome of the recipient organism (ie the sequence coding for this site is not naturally present in the genome of the organism), it is introduced within said genome though any transformation method known in the art, before performing the method of the invention. Thus, the recipient host possesses a "hot spot" for recombination at the place where this site has integrated. It is easy to identify the Y3' and Y5' flanking regions by known methods in the art such as chromosome walking. These methods are not described herein, as the literature already discloses such methods of identifying regions flanking the integration site of a transgene after transformation of a host.

Although dexamethasone is the preferred ligand, it is to be understood that the invention can also be performed with other ligands for the GR-LBD, such as deacylcortivazol, or other agonists. Furthermore, it is well known that some antagonists for this receptor may also have agonist activity under certain circumstances.

The invention also relates to an expression cassette containing a promoter inducible by a steroid, operably linked to a restriction enzyme (site specific endonuclease) coding sequence, said restriction enzyme being preferably a meganuclease as defined above, which may or may not be fused with a rat Glucocorticoid Receptor (GR) Ligand Binding Domain (LBD), as described in the invention. One thus cite a I-SceI meganuclease (SEQ ID No. 5) or the inducible I-SceI protein as described in SEQ ID No. 7. Transformed organisms containing this expression cassette are also subject of the invention.

The term "operably linked" as used herein means that the promoter and the restriction enzyme coding sequence are oriented such that the promoter directs expression of the restriction enzyme coding sequence, generally in the 5'- to 3'-direction. The constructs may also contain polyadenylation sites at the 3'-end of the restriction enzyme coding sequence.

Said promoter is preferably inducible by a glucocorticoid, such as dexamethasone. Steroid action is generally via the action of a steroid receptor that then binds to the promoter.

Once can cite, for example the GVG gene/UAS promoter system, mentioned above, as an indirect inducible promoter system. The GVG gene codes for a modified rat glucocorticoid responsive transcription factor remaining in the cell cytosol as a complex. Upon dexamethasone application, this complex dissociates and the GVG protein enters the nucleus and binds to the target DNA sequences (UAS). Transcription from the UAS promoter allows the production of the restriction enzyme.

Other examples of steroid inducible promoters have been described. One can cite the promoters described by Mader and White (1993), the review of White (1997), the sip48 promoter described by Pruneda-Paz et al (2004), the promoter described by Schena et al (1991).

The expression cassette according to the invention is used to provide the restriction enzyme to perform the Double Strand Break and induce recombination at the breakage site, in particular to excise a specific sequence from the genome or integrate a sequence at a predetermined locus as seen above.

In the case where targeted insertion of a DNA sequence Z is intended, as described above, the expression cassette according to the invention may be present on the same vector that carries said DNA sequence Z.

In the case where excision of a specific DNA sequence is desired in a first plant, as described above, the expression cassette according to the invention may be located within said DNA sequence to be excised, or may be present in a second plant that is crossed to said first plant, thereby providing the restriction enzyme.

The restriction enzymes that are used in the cassette of this embodiment of the invention have been described above. The transformed organisms containing a cassette of this embodiment of the invention are obtained according to methods known in the art. The methods of use of the cassette of this embodiment of the invention (elimination of a sequence in the genome of a target organism, targeted insertion of a sequence at a specific site) have been described above and are performed as described above. In particular, it is preferred that the steroid (preferably dexamethasone) is applied on or just before meiosis.

The present invention will be further understood in view of the annexed figures and following examples.

FIGURES

FIG. 1: Schematic map of the plasmid pBIOS1283. This GATEWAY ENTR plasmid consists of sequence encoding an NLS-I-SceI-GR-LBD fusion protein followed by a CaMV 35S polyadenylation sequence. There is no promoter driving expression of the sequence.

Figure 2:
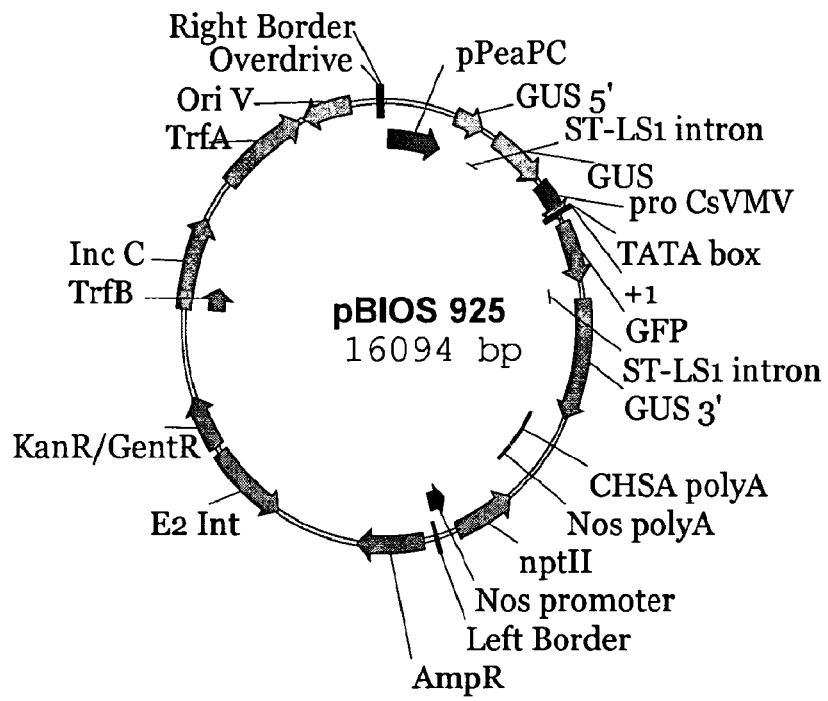

FIG. 2: Schematic diagram of pBIOS925. which is used as an intrachromosomal recombination reporter in *Arabidopsis*.

Figure 3:
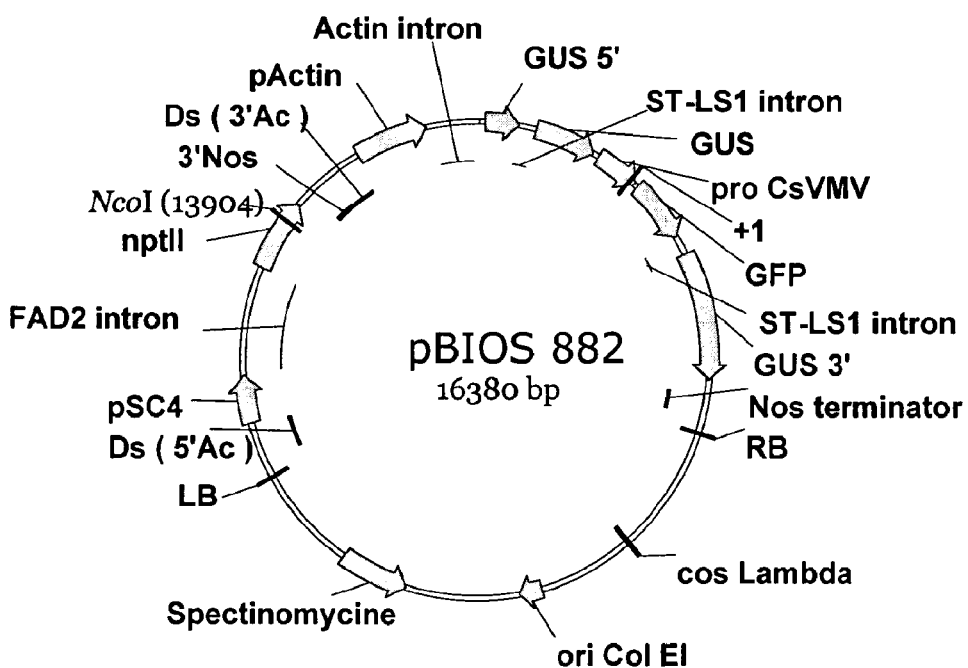

FIG. 3: Schematic diagram of pBIOS882. which is used as an intrachromosomal recombination reporter in maize.

Figure 4:
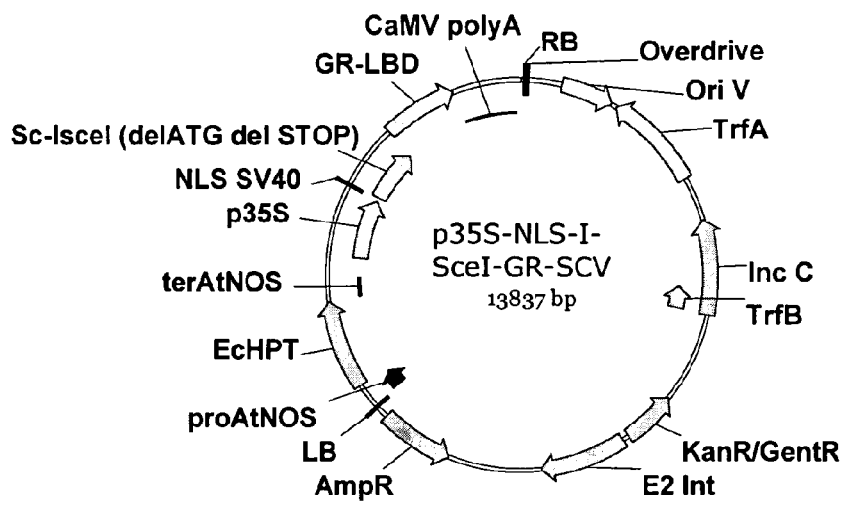

FIG. 4: Schematic diagram of p35S-NLS-I-SceI-GR-SCV (pBIOS1316) which is a binary vector used for the expression of an NLS-I-SceI-GR-LBD fusion protein under the control of the p35S promoter in *Arabidosis*.

Figure 5:
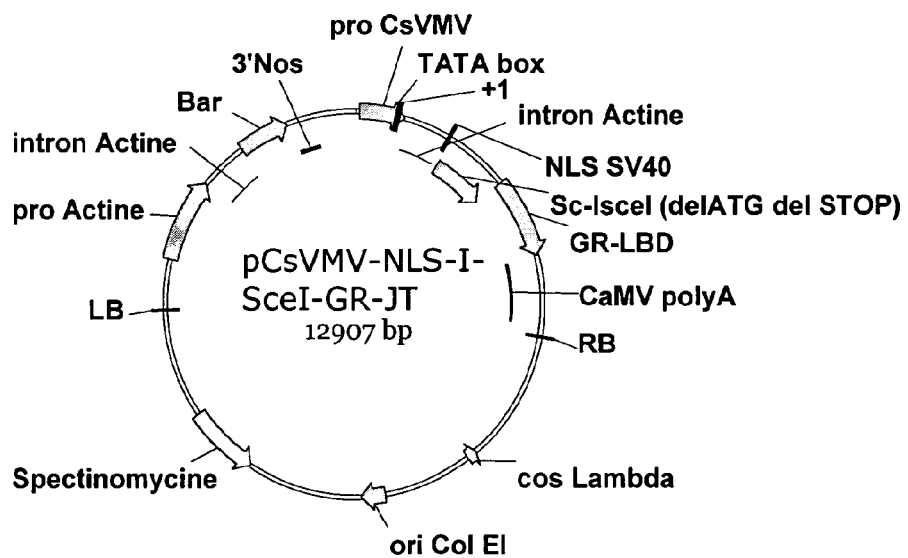

FIG. 5: Schematic diagram of pCsVMV-NLS-I-SceI-GR-JT (pBIOS1371) which is a vector used for the expression of an NLS-I-SceI-GR-LBD fusion protein under the control of the pCsVMV promoter followed by the actin intron in maize.

Figure 6:
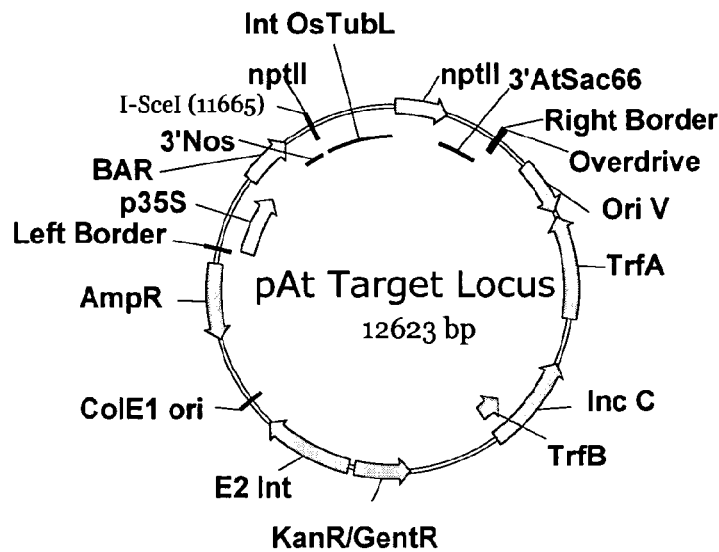

FIG. 6: Schematic diagram of pAt Target Locus, which contains the target locus for GT in *Arabidopsis*.

Figure 7:
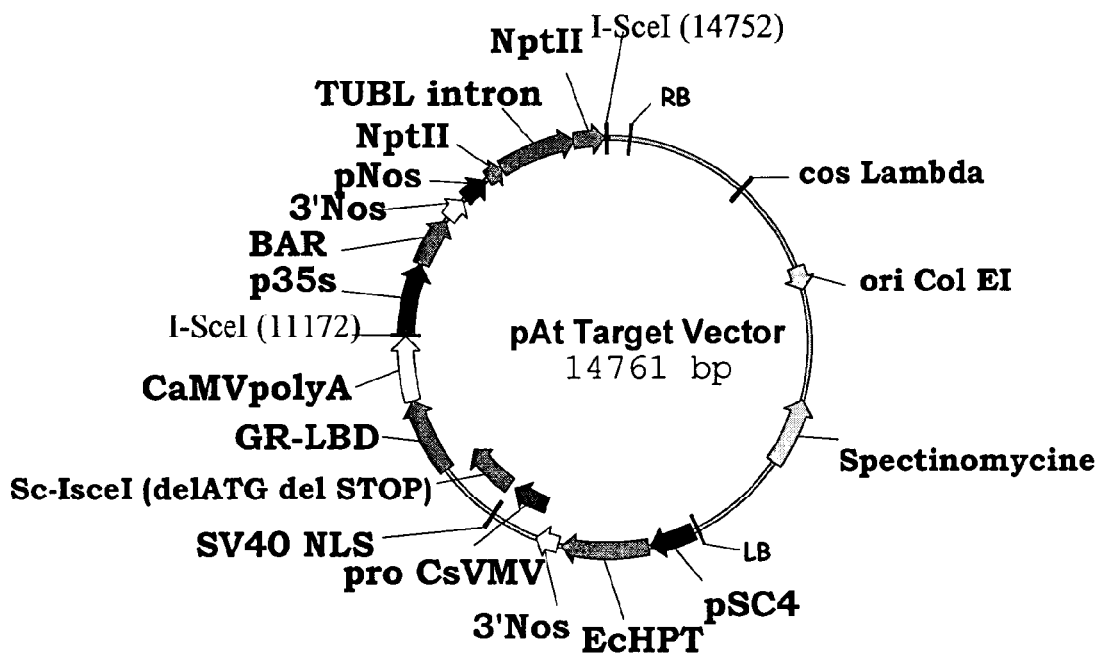

FIG. 7: Schematic diagram of pAt Target Vector which contains the target vector rescue sequence for GT in *Arabidopsis* and the NLS-I-SceI-GR-LBD fusion protein under the control of the p35S promoter.

Figure 8:
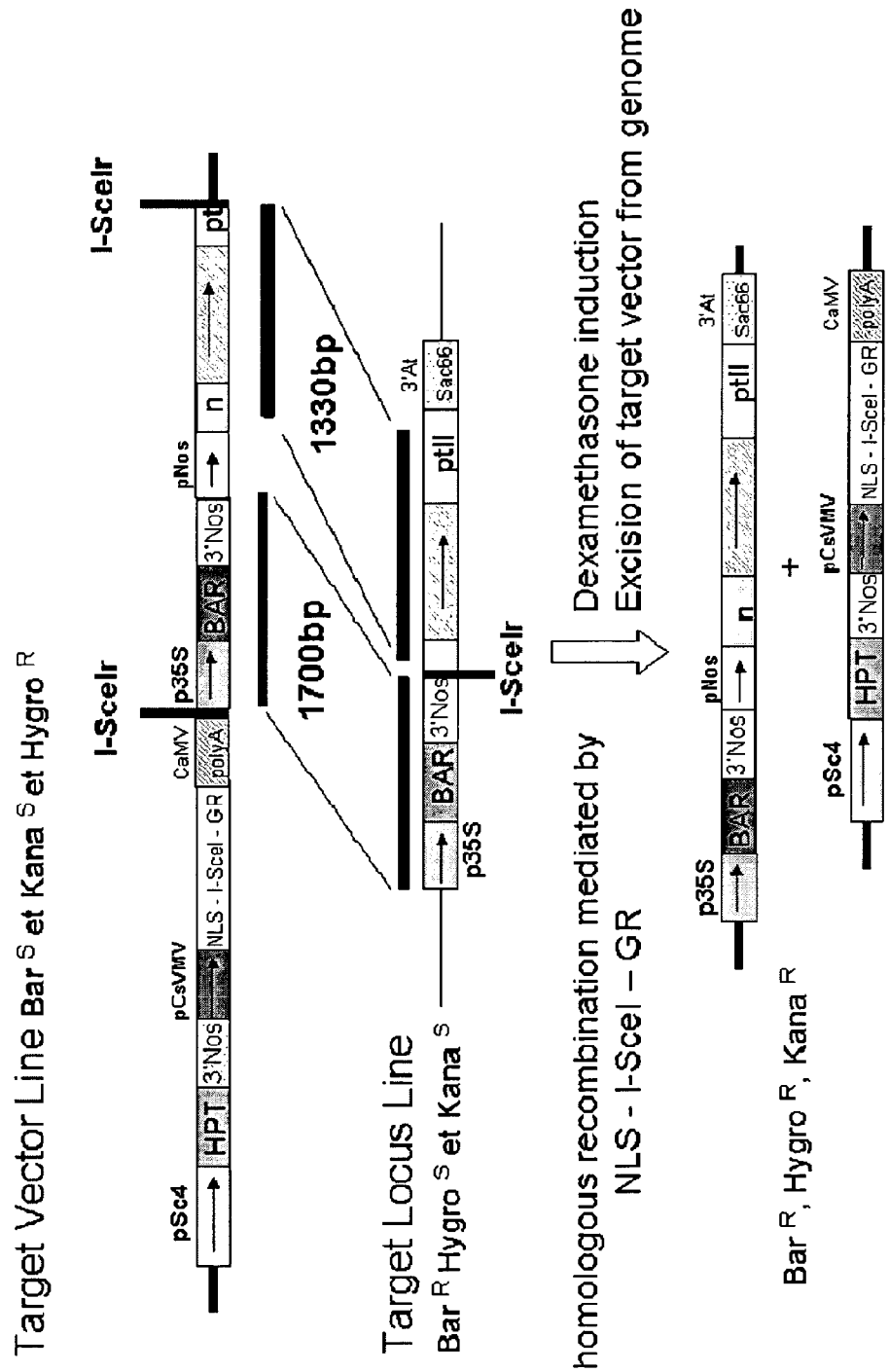

FIG. 8: Schematic diagram of a gene targeting event induced by dexamethasone in *Arabidopsis*.

Figure 9:
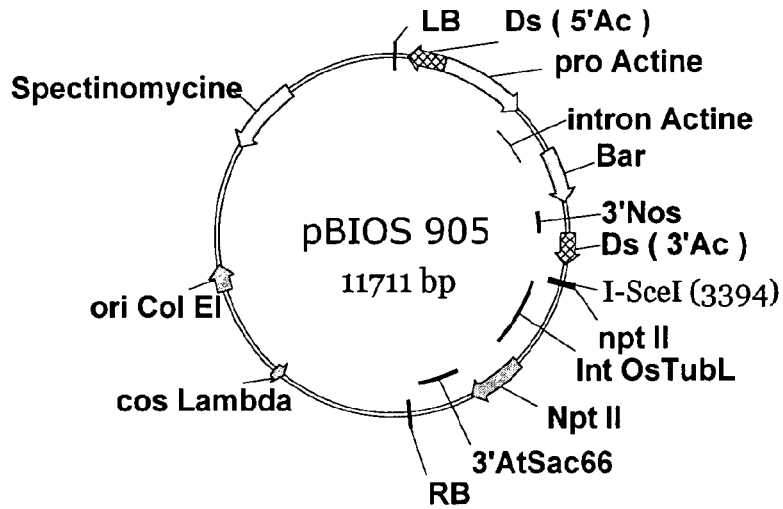

FIG. 9: Schematic diagram of pBIOS905, which contains the target locus for GT in maize.

Figure 10:
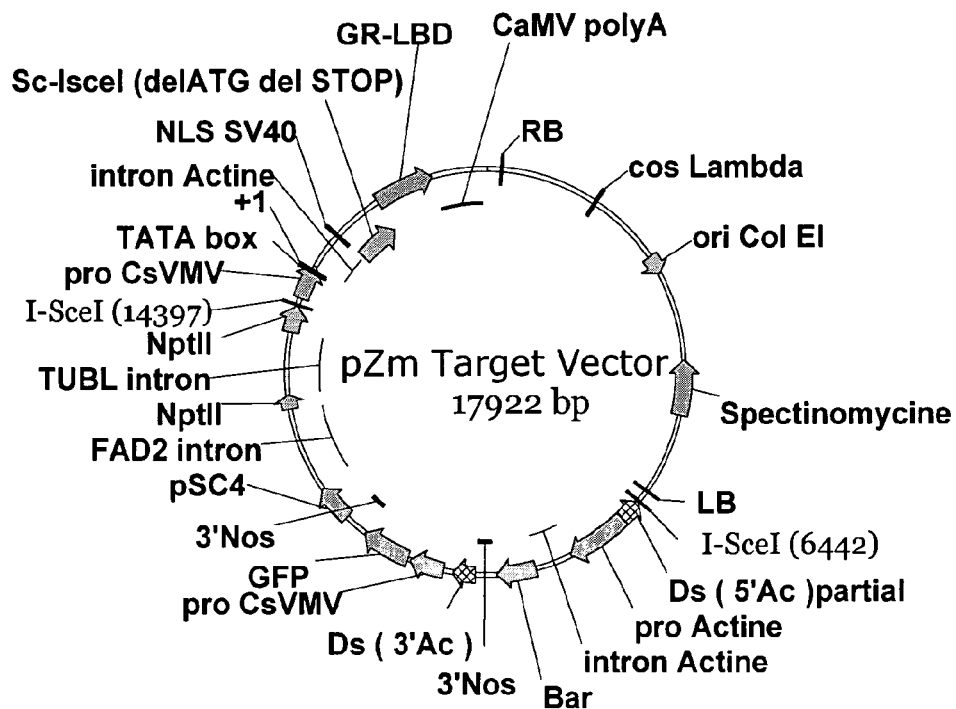

FIG. 10: Schematic diagram of pZm Target Vector (pBIOS1320) which contains the target vector rescue sequence for GT in maize.

Figure 11:
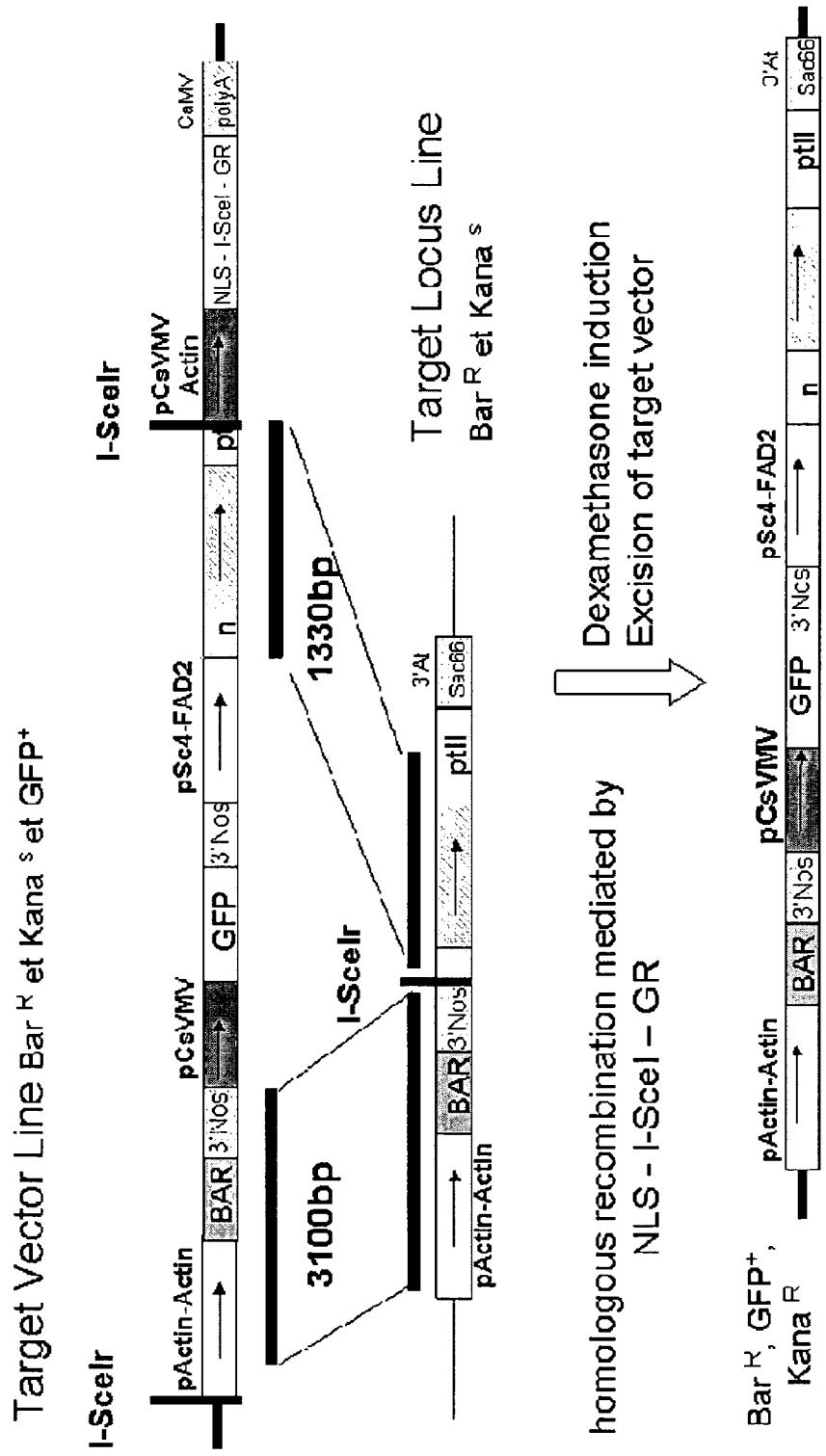

FIG. 11: Schematic diagram of a gene targeting event induced by dexamethasone in maize and the NLS-I-SceI-GR-LBD fusion protein under the control of the pCsVMV promoter followed by the actin intron FIG. 12: Map of the vector used for cis-marker gene elimination using dexamethasone inducible I-SceI expression.

Figure 13:
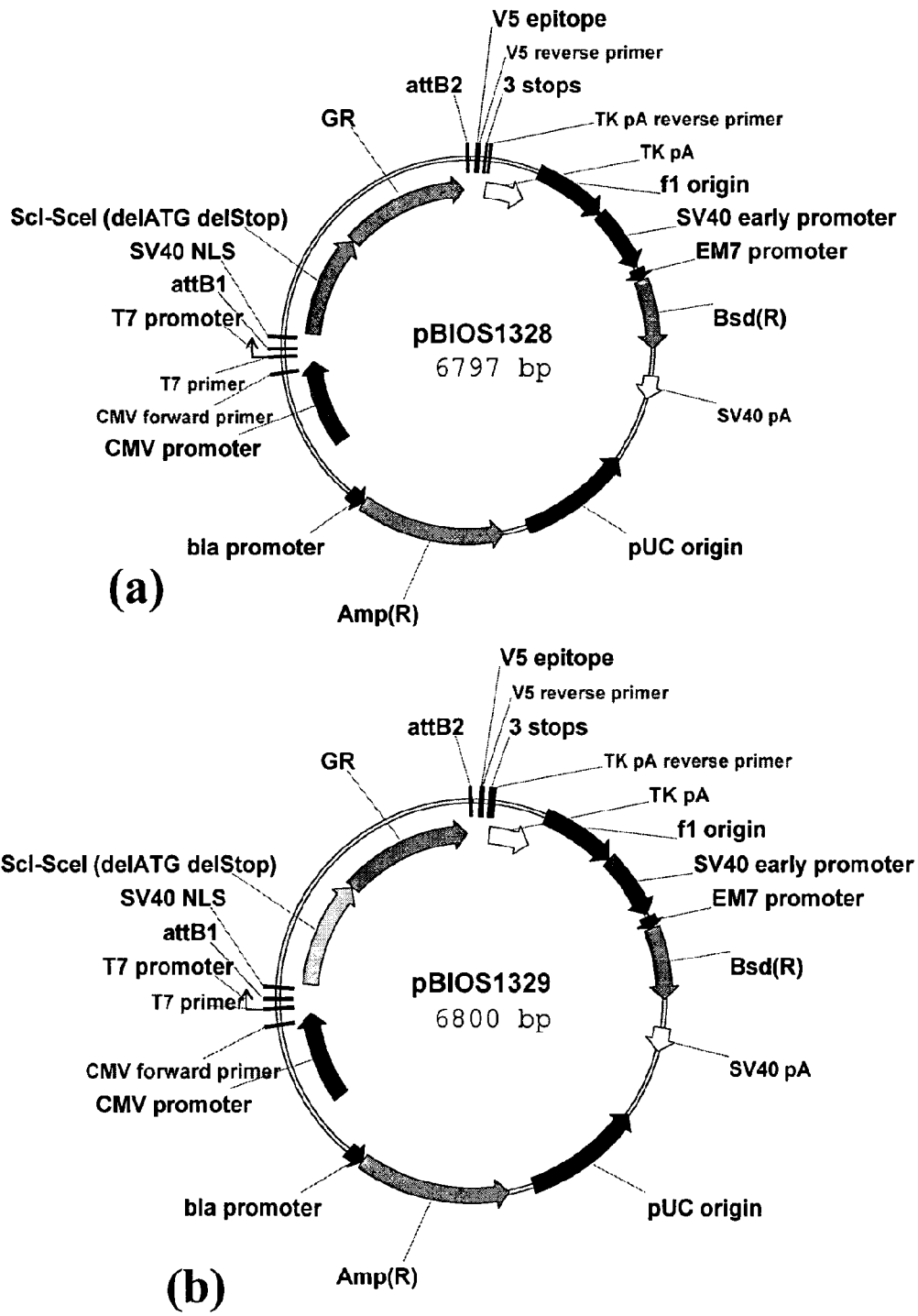

FIG. 13: Schematic diagram of pBIOS1328 (a) and pBIOS1329 (b). pBIOS1329 was constructed by removing the CaMV polyadenylation sequence from pBIOS1283 (FIG. 1). pBIOS1328 (FIG. 13 (a)) is virtually identical to pBIOS1329 apart from lacking a Leucine residue between the NLS and I-SceI domains.

EXAMPLES

The invention will now be described by the way of the following examples, which should not be construed as in any way limiting the scope of the invention.

Example 1

Construction of a DNA Sequence Coding for a Nuclear Targeted, Dexamethasone-Inducible I-SceI Fusion Protein, (SV40NLS-I-SceI-GR LBD)

In order to precisely control the activity of the I-SceI meganuclease the I-SceI coding sequence was modified, as described below, by the 3' addition of a rat glucocorticoid ligand binding domain sequence (Miesfeld et al 1986). The resulting chimeric coding sequence encodes a modified I-SceI protein (I-SceI-GR-LBD) that is only active in the presence of an appropriate chemical inducer such as dexamethasone. The resulting fusion protein is significantly larger than the original I-SceI protein and thus it is possible that transfer of this fusion protein into the nucleus from the cytosol, and thus the access of I-SceI to its target DNA, will be reduced. The addition of a nuclear localisation signal (NLS) to the I-SceI-GR-LBD protein is likely to improve the transfer, after dexamethosone induction, of the fusion protein to the nucleus. The cloning of a NLS-I-SceI-GR-LBD chimeric coding sequence is described below.

A nuclear-encoded meganuclease I-SceI (SEQ ID No. 6) (as in Plessis et al, (1992)), corresponding to the mitochondral group1 intron-encoded endonuclease I-SceI from yeast (Jacquier and Dujon (1985)) was amplified by PCR using modified forward (B_Kz*_NLS_Scl-SceI 5': CATGGATC-CACCATGGCCTGCACCCCGCCGAA-
GAAAAAGAGGAAAGTGCTGGCCAAAAA-
CATCAAAAA) SEQ ID No. 9 and reverse (Scl-SceI3'_SacI (L): CGCGAGCTCTTTCAGGAAAGTTTCGG) SEQ ID No. 10 primers containing BamHI and SacI restriction sites respectively. The forward primer contains downstream of the BamHI site an ATG codon in frame with the SV40 Nuclear Localization Signal (SEQ ID No. 3 and SEQ ID No. 4 as described in Dingwall et al. 1986, Lanford et al. 1984, Kalderson et al, 1984) coding sequence adapted to maize codon usage. The forward primer was also designed in order that the ATG codon of I-SceI is deleted. The reverse primer was designed so that the amplified I-SceI sequence does not contain a stop codon. The PCR fragment was cloned into the pGEM®-T-easy (Promega) vector forming pBIOS1279. The pBIOS1106 vector contains a Rat GR LBD (SEQ ID No. 1, Miesfeld et al. 1986) behind the CaMV polyA terminator. The SV40NLS-I-SceI sequence was excised from pBIOS1279 by restriction digestion with BamHI and SacI. Then the fragment was introduced in pBIOS1106 opened with BamHI and SacI forming a SV40NLS-I-SceI-GR-LBD in frame fusion followed by the CaMV polyA terminator. The resulting plasmid pBIOS1283 is shown in FIG. 1.

Example 2

Construction of Intrachromosomal *Arabidopsis* Reporter Lines for Homologous Recombination (HR)

Intrachromosomal recombination can be used to precisely remove genomic DNA sequences from the genome. In order to demonstrate precise intrachromosomal homologous recombination mediated by the NLS-I-SceI-GR-LBD hormone-inducible fusion protein in *Arabidopsis* the intrachromosomal homologous recombination reporter construct, contained in pBIOS925 (FIG. 2), was introduced into *Arabidopsis*. This reporter construct is composed of a Pea plastocyanin promoter expressed in green tissues (pPeaPC, Pwee et al., 1990) linked to a 3' truncated GUS gene followed by an intervening sequence containing a pCsVMV-GFP gene and a 5' truncated GUS gene. The truncated GUS genes have a 1000 bp region in common such that HR between these GUS duplicated sequences will excise the intervening pCsVMV-GFP gene and precisely reform an entire GUS gene. In addition, between the 3' truncated GUS gene and the CsVMV promoter, there is an I-SceI meganuclease (I-SceIr) restriction site. This allows the creation of an I-SceI-mediated double strand DNA break at this I-SceI-target site. In this and in subsequent examples the GUS gene is used as an example of a gene of interest to be excised in the plant. The details of the construction of pBIOS925 are described below:

A DNA fragment containing an I-SceI restriction site (I-SceIr) was created by annealing two primers RISceI (5'AATTCTAGGGATAACAGGGTAATA 3', SEQ ID No. 11) and H3SceI (5'AGCTTATTACCCTGTTATCCCTAG 3', SEQ ID No. 12). This DNA which contains HindIII and EcoRI compatible overhangs was cloned into HindIII, EcoRI-cut pBS II SK+ (STRATAGENE) forming pBIOS782. The cassette pCsVMV-GFP-Nos from pBIOS411 was inserted as an XhoI, SstII (flushed) fragment, between the XhoI, KpnI (flushed) sites of pBIOS782 forming pBIOS809. (pBIOS411 is a pBSII derivative which contains a CsVMV promoter (Verdaguer et al. (1996)) linked to a GFP (Green Fluorescent Protein) coding sequence followed by a 3'Nos terminator (Depicker A. et al., 1982)) A GUS gene with an STLS1 intron (Vancanneyt G et al., 1990) was introduced between the BamHI and EcoRI sites of pENTR1A (Invitrogen) forming pCL50. The pCsVMV-GFP BamHI, PvuI (flushed) fragment of pBIOS809 was cloned between the BamHI, SnaB1 sites of pCL50 forming the vector pBIOS821. This vector was digested with SmaI and NotI, to extract the cassette 'I-SceIr-pCsVMV-GFP-STLS1 intron-3'GUS' which was introduced between the Csp451 (filled)-NotI sites of pCL50, to obtain the vector pBIOS865. The 'GU-I-SceIr-pCsVMV-GFP-US' region was fused to the pea plastocyanin promoter (pPeaPC) by performing an LR clonase reaction (Invitrogen) with the GATEWAY binary destination vector pPC-R1R2-SCV forming the binary vector pBIOS925 (pPC-R1R2-SCV is a GATEWAY destination plant binary vector containing a pNos-nptII gene for selection of transformed plants, the Pea plastocyanin promoter followed by a GATEWAY cassette and a Chalcone synthase polyadenylation sequence)

pBIOS925 was transferred into agrobacteria, and the *Arabidopsis* cultivar Col4 was transformed with this *Agrobacteria* strain via the floral dip method essentially as described by Clough et al. (1998). The transformed plants were phenotypically normal. Leaves from the transformed plants were examined histochemically for GUS activity. Histochemical detection of GUS expression was performed according to the following method. Plant material was stained in a medium containing 0.5 mg/ml Xglucuronide (Clonetech, Palo Alto, Calif.), 0.5 mM phosphate buffer, pH 7.0, 0.1% triton X-100 and 20% (v/v) methanol. In most transformed plants no GUS staining was observed in leaves. This result confirms that HR (which restores GUS activity), is a rare natural event in *Arabidopsis*.

Example 3

Construction of Intrachromosomal Maize Reporter Lines for Homologous Recombination (HR)

Intrachromosomal recombination can be used to precisely remove genomic DNA sequences from the genome. In order to demonstrate precise intrachromosomal homologous recombination in maize the intrachromosomal reporter construct contained in pBIOS882 (FIG. 3) was introduced into maize. This reporter construct is composed of a constitutive promoter (pActin) linked to a 3' truncated GUS gene followed by an intervening sequence containing a pCsVMV-GFP gene and a 5' truncated GUS gene. The truncated GUS genes have a 1000 bp region in common such that HR between these GUS duplicated sequences will excise the intervening pCsVMV-GFP and precisely reform an entire GUS gene. In addition, between the 3' truncated GUS gene and the CsVMV promoter, there is a restriction site' for the I-SceI meganuclease (I-SceIr). This allows the creation of an I-SceI-mediated double strand DNA break at this I-SceI-target site. In this and in subsequent examples the GFP gene is used as an example of a gene of interest to be excised in the plant, and the GUS gene as an example of a gene that will be made active upon excision of the DNA fragment. The details of the construction of pBIOS882 are described below:—

The 'GU-I-SceIr-pCsVMV-GFP-US' region in pBIOS865 (example 2) was fused to constitutive rice Actin promoter plus a rice Actin intron by performing an LR clonase reaction (Invitrogen) with the GATEWAY binary destination vector pWP527-R12-JTT forming the binary vector pBIOS 882. (The vector pWP527-R12-JTT is a derivative of pSB11 (Komari et al. (1996)) containing a pSc4 (Boevink, P et al., 1995). -NptII (Bevan M W, 1992; Berg et Berg, 1983) gene for selection of maize transformants, a rice pActin promoter linked to a rice actin intron in front of a GATEWAY cassette).

pBIOS 882 was transferred into agrobacteria LBA4404 (pSB1) according to Komari et al. (1996) and the Maize cultivar A188 was transformed with this agrobacterial strain essentially as described by Ishida et al. (1996). The transformed plants were phenotypically normal. Pollen from the transformed plants was examined histochemically for GUS activity. Histochemical detection of GUS expression was performed according to the following method. Plant material was stained in a medium containing 0.5 mg/ml Xglucuronide (Clonetech, Palo Alto, Calif.), 0.5 mM phosphate buffer, pH 7.0, 0.1% triton X-100 and 20% (v/v) methanol. In most transformants no GUS staining was observed in roots leaves and pollen though in 2 plants a few GUS stained pollen grains were observed. This result confirms that HR (which restores GUS activity), is a rare natural event in maize.

Example 4

Intrachromosomal Recombination and Removal of Intergenic DNA Sequences in *Arabidopsis* Mediated by the Dexamethasone-Inducible NLS-I-SceI-GR-LBD Fusion Protein In order to assess the effect of inducible NLS-I-SceI-GR-LBD fusion protein expression on the frequency of HR-mediated DNA excision, *Arabidopsis* plants containing the intrachromosomal HR reporter (example 2) are retransformed with a p35S CaMV-NLS-I-SceI-GR LBD transgene. This transgene is constructed by introducing the CaMV 35S promoter (p35S) upstream of the NLS-I-SceI-GR-LBD fusion in pBIOS1283 (example 1). The resulting chimeric p35S-NLS-I-SceI-GE-LBD-CaMVpolyA gene is transferred into the plant binary vector pBIOS1110 via an LR clonase reaction forming the vector p35S-NLS-I-SceI-GR-SCV (pBIOS1316, FIG. 4) (pBIOS1110 is a derivative of the plant binary vector pSCV1 containing a pNos-HPT selectable marker gene and a GATEWAY cassette). The plasmid p35S-NLS-I-ISceI-GR-SCV (pBIOS1316) is introduced into *Agrobacteria*, and the *Arabidopsis* lines described in example 2 are retransformed with this *Agrobacteria* strain essentially as described by Clough et al. (1998). The transformed plants are phenotypically normal. T1 plants containing both the I-SceI inducible system and the reporter sequences are selected. Then *Arabidopsis* buds of different developmental stages (<0.5 to 1 mm long) are infiltrated under vacuum in a dexamethasone solution (30 µM) (buds are used since ideally the targeting vector is excised by the NLS-I-SceI-GR-LBD protein and available as a substrate for HR during meiosis). The progeny of those plants and the progeny of dexamethasone untreated plants are analyzed at the seedling stage for GUS activity histochemically. Such analysis provides an estimate of the frequency of intrachromosomal HR giving rise to excision of the pCsVMV-GFP gene and the reconstitution of the GUS gene. The rate of DNA excision (totally blue plantlets) obtained under dexamethasone treatment is higher that without dexamethasone. This demonstrates that recombination, leading to DNA excision, mediated by the NLS-I-SceI-GR LBD fusion protein is induced by dexamethasone treatment.

Example 5

NLS-I-SceI-GR LBD Fusion Protein-Mediated Stimulation of Intrachromosomal HR and Removal of Intergenic DNA Sequences in Maize In order to assess the effect of inducible NLS-I-SceI-GR-LBD fusion protein expression on the frequency of HR-mediated DNA excision, maize plants are transformed with a vector designed for the expression of the NLS-I-SceI-GR LBD fusion protein in maize. This vector is constructed by introducing the constitutive Cassaya Vein Mosaic Virus (pCsVMV) promoter ((Verdaguer et al. (1996)), linked to an actin intron (McElroy et al. (1990)), upstream of the NLS-I-SceI-GR LBD fusion (example 1). The created chimeric gene is then transferred via an LR clonase reaction into the binary vector pBIOS605. (The vector pBIOS605 is a derivative of pSB11 (Komari et al. (1996)) containing a pActin-Bar gene for selection of maize transformants, and a GATEWAY cassette). The resultant expression clone pCsVMV-NLS-I-SceI-GR-JT (pBIOS1371, FIG. 5) obtained is introduced into the agrobacteria strain LBA4404 (pSB1) according to Komari et al (1996). Maize cultivar A188 is transformed with this agrobacterial strain essentially as described by Ishida et al. (1996). The transformed plants are phenotypically normal. T1 plants which express the NLS-I-SceI-GR-LBD gene are selected by RT-PCR and crossed with intramolecular HR reporter plants described in example 3. Progeny of those plants containing both the NLS-I-SceI-GR LBD gene and the reporter gene are selected and a proportion of these plants are treated with a solution of dexamethasone (a range around 30 µM is used) applied as drops into the whorl on those plants. Dexamethasone treatment is repeated each 2 days between 10 to 40 days after sowing. Ideally dexamethosone should be applied just prior to the stage of meiosis such that the targeting vector is excised by the NLS-I-SceI-GR-LBD protein and available as a substrate for HR during meiosis. This is since it is likely that RH is favoured during meiosis. The mature pollen of dexamethasone treated and untreated plants are analyzed for GUS activity histochemically since such analysis provides an estimate of the frequency of intrachromosomal HR giving rise to excision of the pCsVMV-GFP gene and the reconstitution of the GUS gene.

The DNA excision activity and thus frequency of GUS staining, was substantially greater in pollen of lines treated with dexamethasone than in untreated lines. This demonstrates a stimulation of HR and DNA excision in the presence of dexamethasone-induction of NLS-I-SceI-GR LBD expression.

Example 6

Inducible-I-Sce-I Expression to Mediate Gene Targeting in *Arabidopsis*

It is highly desirable to be able to insert exogenous DNA into a defined site in the plant genome or replace defined DNA sequences 'gene targeting' using homologous recombination. A barrier to the use of HR for gene targeting is the inefficiency of HR in plants, particularly the fact that at a DNA double strand break the competing non homologous end joining mechanism (NHEJ) predominates in most plant tissues. This inefficiency of HR leads to a need to produce many thousands of plant transformation events to find a single HR gene targeting event. In plant species where transformation rates are low this prevents the routine use of HR for gene targeting. A solution is to produce a stably transformed plant line where the DNA substrate for HR mediated gene targeting 'Target Vector' can be made available by induction of I-SceI activity. This plant line can be multiplied indefinitely in the absence of induction and a large population of I-SceI induced plants can be screened for rare HR gene targeting events. This approach is exemplified in *Arabidopsis* using HR-mediated gene targeting to reconstitute an inactive 5' truncated nptII gene, though the approach can be applied to target endogenous genes. In this case only the 'Target Vector' needs to be transformed into *Arabidopsis*.

Construction of the 'Target Locus' *Arabidopsis*' Line

*Arabidopsis* is transformed with the construct pAtTarget-Locus (FIG. 6). This binary plasmid consists of the following components in the T-DNA; next to the T-DNA left border is the p35S-BAR-nospolyA selectable marker gene that is required for plant transformation and also to act as a region with homology to the Target Vector, followed by a restriction site for I-SceI. 3' of this I-SceI site is a 5' truncated nptII gene followed by a nospolyA sequence and the T-DNA right border. This nptII gene contains a rice tubulin intron such that the region of homology with the target vector is extended (FIG. 8).

pAtTargetLocus is transferred to agrobacteria and is transformed into *Arabidopsis* using a floral dip method (Clough et al., 1998). Tranformants (T0) are selected on BASTA and selfed for two generations. T2 lines homozygous for a single copy of the T-DNA are selected and the integrity of the T-DNA verified by PCR and Southern analysis. The selected lines do not display kanamycin resistance.

Construction of the 'Target Vector'

The binary plasmid pAtTargetVector consists of the following components in the T-DNA; next to the T-DNA left border is a pSc4-Hyg-nosPolyA selectable marker gene, a pCsVMV-NLS-I-SceI_GR-LBD chimeric gene followed by a restriction site for I-SceI, the p35S-BAR-nospolyA gene, that is required for to act as a region with homology to the Target Locus, the nos promoter linked to the 5' region of the nptII intron gene followed by a restriction site for I-SceI and the T-DNA right border (FIG. 7).

pAtTargetVector is transferred to agrobacteria and is transformed into the selected *Arabidopsis* Target Locus lines using a floral dip method (Clough et al., 1998). Tranformants (T0) are selected on hygromycin and selfed for two generations. T2 lines homozygous for a single copy of the TargetLocus and TargetVector T-DNAs are selected, and the integrity of the T-DNA verified by PCR and Southern analysis. The selected lines do not display kanamycin resistance.

Induction of GeneTargeting

T3 *Arabidopsis* buds of different developmental stages (<0.5 to 1 mm long). are infiltrated under vacuum in a dexamethasone solution (30 µM). (Dexamethosone treatment induces I-SceI activity and both excises the Target Vector from the genome and creates a DSB at the Target Locus. The Target Vector can then recombine via HR at the Target Locus and reconstitute a functional nptII gene (FIG. 8). Ideally dexamethosone should be applied just prior to the stage of meiosis such that the targeting vector is excised by the NLS-I-SceI-GR-LBD protein and available as a substrate for HR during meiosis. This is since it is likely that RH is favoured during meiosis. The progeny of those plants and the progeny of dexamethasone untreated plants are analyzed at the seedling stage for resistance to nptII. The frequency of nptII resistant plantlets is obtained under dexamethasone treatment is clearly higher than without dexamethasone. Southern analysis of several nptII resistant plants demonstrated precise reconstitution of a functional nptII gene at the TargetLocus. This demonstrates that gene targeting mediated by the NLS-I-SceI-GR LBD fusion protein is induced by dexamethasone treatment.

Example 7

Inducible-I-Sce-I Expression to Mediate Gene Targeting in Maize

It is highly desirable to be able to insert exogenous DNA into a defined site in the plant genome or replace defined DNA sequences 'gene targeting' using homologous recombination. A barrier to the use of HR for gene targeting is the inefficiency of HR in plants, particularly the fact that at a DNA double strand break the competing non homologous end joining mechanism (NHEJ) predominates in most plant tissues. This inefficiency of HR leads to a need to produce many thousands of plant transformation events to find a single HR gene targeting event. In maize where transformation rates are low this prevents the routine use of HR for gene targeting. A solution is to produce a stably transformed plant line where the DNA substrate for HR mediated gene targeting 'Target Vector' can be made available by induction of I-SceI activity. This maize line can be multiplied indefinitely in the absence of induction and a large population of I-SceI induced plants can be screened for rare HR gene targeting events. This approach is exemplified in maize using HR-mediated gene targeting to reconstitute an inactive 5' truncated nptII gene, though the approach can be applied to target endogenous genes. In this case only the 'Target Vector' needs to be transformed into maize.

Construction of the 'Target Locus' Maize Line

Maize was transformed with the construct pBIOS905. This binary plasmid consists of the following components in the T-DNA; next to the T-DNA left border is the pActin-actin intron-BAR-nospolyA selectable marker gene that is required for plant transformation and also to act as a region with homology to the Target Vector, followed by a restriction site for I-SceI. 3' of this I-SceI site is a 5' truncated nptII gene followed by an AtSac66polyA sequence and the T-DNA right border (FIG. 9). This nptII gene contains a rice tubulin intron such that the region of homology with the target vector is extended.

pBIOS905 was transferred into agrobacteria LBA4404 (pSB1) according to Komari et al. (1996) and the Maize cultivar A188 was transformed with this agrobacterial strain essentially as described by Ishida et al. (1996). The transformed plants were phenotypically normal. Tranformants (T0) were selected on BASTA and selfed for two generations. T2 lines homozygous for a single copy of the T-DNA were selected, and the integrity of the T-DNA verified by PCR and Southern analysis. The selected lines did not display kanamycin resistance.

Construction of the 'Target Vector'

The binary plasmid pZmTargetVector (pBIOS1320) consists of the following components in the T-DNA; next to the T-DNA left border is a restriction site for I-SceI, the pActin-actin intron-BAR-nospolyA gene, that is required as a selectable marker for plant transformation and to act as a region with homology to the Target Locus, the pCsVMV promoter linked to GFP which is a marker for the T-DNA the pSc4 promoter linked to a FAD2 intron and the 5' region of the nptII intron gene followed by a pCsVMV-NLS-I-SceI_GR-LBD chimeric gene, a restriction site for I-SceI and the T-DNA right border (pBIOS1320, FIG. 10).

pBIOS1320 is transferred into agrobacteria LBA4404 (pSB1) according to Komari et al. (1996) and the Maize cultivar A188 is transformed with this agrobacterial strain essentially as described by Ishida et al. (1996). The transformed plants are phenotypically normal. Tranformants (T0) are selected on BASTA and selfed for two generations. T2 lines homozygous for a single copy of the T-DNA are selected and the integrity of the T-DNA verified by PCR and Southern analysis. The selected lines do not display kanamycin resistance.

Induction of GeneTargeting

Homozygous TargetLoci and TargetVector Lines are crossed and a proportion of the progeny are treated with a solution of dexamethasone (range around 30 µM) applied as drops into the whorl on those plants. Dexamethasone treatment is repeated each 2 days between 10 to 40 days after sowing (Dexamethasone treatment induces I-SceI activity and both excises the Target Vector from the genome and creates a DSB at the Target Locus. The Target Vector can then recombine via HR at the Target Locus and reconstitute a functional nptII gene (FIG. 11). Ideally dexamethasone should be applied just prior to the stage of meiosis such that the targeting vector is excised by the NLS-I-SceI-GR-LBD protein and available as a substrate for HR during meiosis. This is since it is likely that RH is favoured during meiosis). The progeny of those plants and the progeny of dexamethasone untreated plants are analyzed at the plantlet stage for kanamycin resistance by leaf painting with a solution of kanamycin and via PCR to identify a reconstituted nptII gene. The frequency of nptII resistant plantlets is obtained under dexamethasone treatment is clearly higher than without dexamethasone. Southern analysis of several nptII resistant plants demonstrated precise reconstitution of a functional nptII gene at the TargetLocus. This demonstrates that gene targeting mediated by the NLS-I-SceI-GR LBD fusion protein is induced by dexamethasone treatment.

Example 8

Construction of Intrachromosomal Maize Reporter Lines for Inducible HR and NHEJ Mediated by Inducible I-SceI Expression and Cis-Elimination of the Selectable Marker and I-SceI Genes When a marker gene is to be eliminated and a non-inducible I-SceI is to be expressed, it is preferable to control its expression in T0 plants such that it is expressed after the period where selectable marker gene expression is required.

In this example a dexamethasone inducible promoter is used to control I-SceI expression (Aoyama and Chua (1997)). The application of dexamethosone induces I-SceI expression and the I-SceI gene together with the plant selectable marker is excised from the genome.

Figure 12:
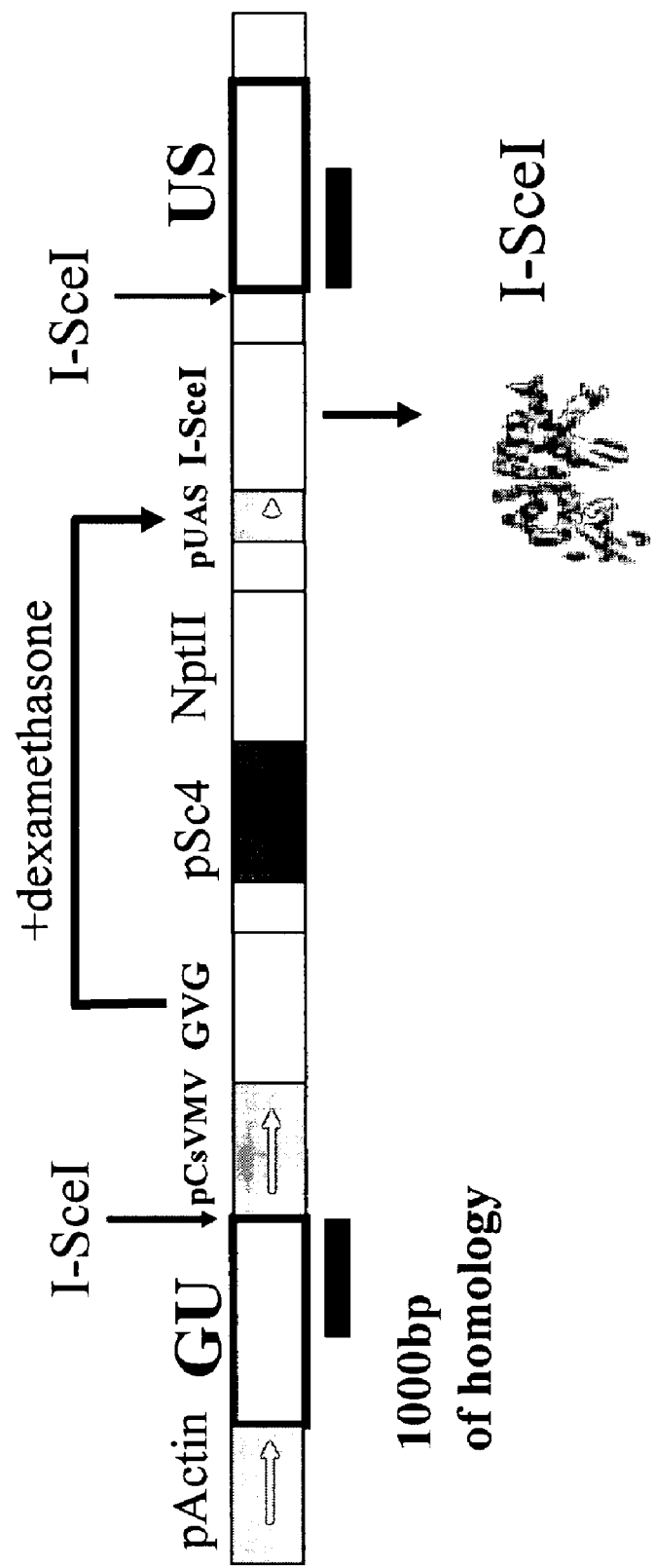

The following genes are cloned between two I-SceI sites:— pCsVMV-GVG+pSc4-FAD2int-nptII+pUAS-I-SceI. (The GVG gene product is a modified rat glucocorticoid responsive transcription factor that remains in the plant cytosol as a complex and is described in numerous articles, together with the pUAS promoter. On dexamethasone application this complex dissociates such that the GVG protein enters the nucleus and binds to the target DNA sequences (UAS). Transcription from the UAS promoter allows the production of I-SceI.) The GVG+nptII+I-SceI region is cloned as an I-SceI fragment into I-SceI-cut pBIOS881. The 5'GUS-I-SceIr-pCsVMV-I-GVG+pSc4-FAD2int-nptII+pUAS-I-SceI 3'GUS region is transferred via an LR clonase reaction into a GATEWAY binary destination vector that is a pSB11 derivative containing an Actin promoter followed by a GATEWAY cassette (FIG. 12).

The resulting plasmid is transferred into agrobacteria LBA4404 (pSB1) according to Komari et al. (1996) and the Maize cultivar A188 is transformed with this agrobacterial strain essentially as described by Ishida et al. (1996). T0 plantlets are either transferred to a medium containing dexamethasone then later transferred to soil. Alternatively, T0 plants are watered with or injected with a solution of dexamethasone. Pollen from dexamethasone treated transformed plants is examined histochemically for GUS activity, to check that, in most transformants, GUS staining is observed at a high frequency. The pollen is then used to fertilize a wild-type plant and obtain F1 progeny that express GUS in all tissues but do not contain the I-SceI or nptII genes.

Example 9

Intrachromosomal Recombination and Removal of Intergenic DNA Sequences from a PAT-PAT Transgene in *Arabidopsis* Mediated by the Dexamethasone-Inducible NLS-I-SceI-GR-LBD Fusion Protein An *Arabidopsis* intrachromosomal HR reporter line is used in this example, which contains a T-DNA called PAT-PAT. This T-DNA is composed of two mutated phosphinothricin acetyltransferase (PAT) genes (Block et al 1987), under the control of a 35S promoter and a Nos terminator. This construct was provided by F. Degroote and G. Picard (UMR CNRS/UBP 6547, unpublished). These mutated PAT genes do not produce the functional enzyme which confers glufosinate resistance. An I-SceI restriction site and an NptII gene, under the control of a pNos promoter and a Nos terminator are present between the two mutated PAT genes.

The vector pBIOS1316 containing the 35S-NLS-I-SceI-GR-LBD chimaeric gene (example 4, FIG. 4) was introduced into *Agrobacteria*, and the *Arabidopsis* reporter lines were transformed with this *Agrobacteria* strain essentially as described by Clough et al. (1998). The transformed plants were phenotypically normal. T1 plants containing both the I-SceI inducible system and the reporter sequences were selected.

Northern Blots were performed on these T1 plants to investigate the level of transcripts expression.

The T2 seeds were treated as follows:
500 seeds were sown on media, containing Glufosinate.
500 seeds were sown on a media, containing Glufosinate and dexamethasone 30 µM.

Results show clearly a difference with and without dexamethasone (Table I).

In the presence of dexamethasone, there are more herbicide resistant plantlets than in the absence of dexamethasone treatment (basal level of intrachromosomal HR).

Such herbicide resistance is due to intrachromosomal HR between the 2 mutated PAT genes reconstituting a functional PAT gene and, in most cases, eliminating the region between the two PAT genes including the nptII gene.

TABLE I number of plants resistant to glufosinate (GlufoR) in the presence or in absence of induction with dexamethasone

| GlufoR plants | Control | Line 1 | Line 2 | Line 3 | Line 4 |
| --- | --- | --- | --- | --- | --- |
| without dexamethasone | 0 | 27 | 8 | 2 | 18 |
| with dexamethasone | 0 | 250 | 320 | 68 | 252 |
| Induction factor | 0 | ×9 | ×40 | ×34 | ×14 |

It is to be noted that, for some other events, the stimulation of intrachromosomal HR in the presence of dexamethasone was as high as 80 fold (not shown).

REFERENCES

Aggarwal A K, Wah D A. (1998) Curr Opin Struct Biol. February; 8(1):19-25.
An et al. (1986), Plant Physiology, 81:86-91
Aoyama T, Chua N H. (1997). Plant J. 11:605-12.
Araki H et al. (1985) J Mol Biol. 182:191-203.
Babwah A. V., Waddell C. S. (2000). Theor. Appl Genet. 100:802-809.
Bansal K C et al. (1992) Proc Natl Acad Sci USA. April 15; 89(8):3654-8.
Baran G, Echt C, Bureau T, Wessler S. (1992). Genetics. February; 130(2):377-84.
Bechtold N, Ellis J, Pelletier G. (1993) C R Acad Sci III. 316(10): 1194-1199
Bevan et al. (1983), Nature, 304:184-187
Berg et Berg, (1983), Biotechnology 1: 417-435
Bevan M W et al. (1992). Biotechnology. 1992 24:367-70
Bleuyard J Y, White C I. (2004) EMBO J. January 28; 23(2): 439-49.
Block et al (1987) EMBO J. 6: 2513-2518.
Boevink, P., Chu, P. W. and Keese, P. (1995) Virology 207 (2), 354-361
Boyko A, Zemp F, Filkowski J, Kovalchuk I. (2006) Plant Physiol. February 10;
Boyko A et al. (2006) Mutat Res. January 25
Boyko A, Filkowski J, Kovalchuk I. (2005) Mutat Res. May 2; 572(1-2):73-83
Broach J R, Guarascio V R, Jayaram M. (1982). Cell. 29:227-34.
Brocard J et al. Nucleic Acids Research, 1998, Vol. 26, No. 17
Chiurazzi M et al. (1996) Plant Cell. 8:2057-66.
Christensen A H, Quail P H. (1996) Transgenic Res. May; 5(3):213-8.
Choulika A, et al. (1994) C R Acad Sci III. November; 317 (11):1013-9.
Choulika A, et al. (1995) Mol Cell Biol. April; 15(4):1968-73.
Chupeau, M C et al (1989). Biotechnology vol. 7: pp. 503-508
Clough S J, Bent A F. (1998). Plant J; 16:735-43.

Coppoolse E R et al. (2003) Plant Mol Biol. 51:263-79.
Dekeyser et al. (1988), Plant Physiology, 90:217-223
De Neve M et al. (1997). Plant J. 11:15-29.
Depicker A et al. (1982) J Mol Appl Genet. 1:561-73.
Depigny-This D, et al. (1992), Plant Mol Biol.; 20(3):467-79.
Dingwall C. et al (1986), Cell Biol. 2, 367-390.
Doutriaux et al. (1998) Mol Gen Genet. February; 257(3): 283-91.
Dubouzet et al. (2003) Plant J. 2003 February; 33(4):751-63.
Ebinuma H et al. (2005). Methods Mol Biol. 286:237-54.
Eichholtz D A et al. (1987), Somat Cell Mol Genet. January; 13(1):67-76
Erikson O., et al. (2004). Nat Biotechnol. April; 22(4):455-8
Finer J. (1992) Plant Cell Report 11: 323-328.
Fromm M E et al. (1986) Nature. February 27-March 5; 319(6056):791-3.
Goldsbrough A P et al. (1993). Bio/Technology 11:1286-1292.
Gritz L, Davies J. (1983), Gene. November; 25(2-3):179-88.
Guerche P, et al. (1987), Biochimie. June-July; 69(6-7):621-8.
Hauptmann et al. (1988), Plant Physiology, 86:602-606
Hoess R H, et al. (1982) Proc Natl Acad Sci USA. 79:3398-402.
Hohn B, Levy A A, Puchta H. (2001). Curr Opin Biotechnol. 12:139-43.
Iida S, Terada R. (2005) Plant Mol Biol. 2005 September; 59(1):205-19.
Ishida Y et al. (1996) Nature Biotechnol. 14, 745-50.
Jacquier, A. and Dujon, B. (1985). Cell 41, 383-394.
Jefferson, R. A., et al. (1987). EMBO J 6, 3901-3907.
Jefferson R A. (1989). The GUS reporter gene system. Nature. 342:837-8.
Jenkins E et al. (1999) Plant Cell Environ 22: 159-167
Kaiser J (2005) Putting the finger on gene repair. Science 310: 1894-1896.
Kalderson D. et al. (1984) Nature 311, 33-38.
Kathiresan, A. et al. (2002) Sex. Plant Reprod. 14, 257-267
Kay et al. (1987), Science, 236:1299-1302
Kerbach S, Lorz H, Becker D. (2005) Theor Appl Genet. 111:1608-16.
Klimyuk V I, Jones J D. (1997) Plant J. January; 11(1):1-14.
Kizis D, Pages M. (2002) Plant J. June; 30(6):679-89.
Koo J C et al. (2004) Plant J. February; 37(3):439-48.
Komari T et al. (1996) Plant J. 10:165-74.
Lanford R. E., Butel J. S., (1984) Cell 37, 801-813
Lee S C et al. (2004) Mol Cells. August 31; 18(1):107-14.
Lyznik L A, Rao K V, Hodges T K. (1996) Nucleic Acids Res. 24:3784-9.
Mader S, White J H, (1993) Proc Natl Acad Sci USA. 90(12): 5603-5607
Marshall P, Lemieux C. (1991) Gene. August 15; 104(2):241-5.
Matsuoka M et al. (1994) Plant J. September; 6(3):311-9.
McElroy, D. Zhang, W. Cao, J. Wu, R. (1990) Plant Cell 2(2):163
McElroy D, Blowers A D, Jenes B, Wu R. (1991) Mol Gen Genet. 1:150-60.
Meijer E G et al. (1991), Plant Mol Biol. 1991 May; 16(5): 807-20.
Miesfeld R. et al. (1986) Cell 46 (3), 389-399.
Miki B., McHugh S. (2004) Journal of Biotechnology 107: 193-232
Monnat Jr et al. (1999) Biochem Biophys Res Commun. February 5; 255(1):88-93.
Morita R et al. (2003) Plant Cell Physiol. 44:637-42.
Moore I et al. (2006) Plant J. 45:651-83.
Mukhopadhyay A, et al. (2004) Proc Natl Acad Sci USA.; 101(16):6309-14.
Mundy J, Chua N H. (1988) EMBO J. 1988 August; 7(8): 2279-86.
Nielsen K., et al. (1999) Physiological and Molecular Plant Pathology 54, 1-12
Orel N, Kyryk A, Puchta H. (2003). Plant J. 35:604-12.
Padidam M. (2003) Curr Opin Plant Biol. April; 6(2):169-77.
Pellegrineschi A et al. (2004) Genome. June; 47(3):493-500.
Pwee K-H and Grey J C (1990) Plant Journal 3, 4370-4449
Plessis A, et al. (1992). Genetics 130, 451-60.
Potenza C, et al. (2004) In Vitro Cell. Dev. Biol. 40:1-22.
Pruneda-Paz J L, et al. (2004) J Steroid Biochem Mol Biol; 88(1):91-100
Puchta H. (2003). J Plant Physiol. 160:743-54.
Que Q. (2005) 47th Maize Genetics Conference, Mar. 10-13, 2005
Rabbani M A et al. (2003) Plant Physiol. December; 133(4): 1755-67.
Raeymaekers L. (1993) Anal Biochem. November 1; 214(2): 582-5.
Radhakrishnan P, Srivastava V. (2005) Plant Cell Rep. 23:721-6.
Roslan H A et al. (2001) Plant J. October; 28(2):225-35.
Russell D A, Fromm M E. (1997) Transgenic Res. March; 6(2):157-68.
Saijo Y et al. (2000) Plant J. August; 23(3):319-27.
Saidi Y et al. (2005) Plant Mol Biol. 2005 November; 59(5): 697-711.
Scott L, LaFoe D, Weil C F. (1996) Genetics. January; 142 (1):237-46.
Sambrook J. et Russell D. W. (2001) "Molecular Cloning—A laboratory Manual, third edition", chapitre 1.1, Editeur.: CSHL Press
Schena et al. (1991) Proc Natl Acad Sci USA, Vol. 88, No. 23, pp 10421-25
Severin K, Schoffl F. (1990) Plant Mol Biol. December; 15(6):827-33.
Shen Q, Uknes S J, Ho T H. (1993) J Biol Chem. November 5; 268(31):23652-60.
Siebert R, Puchta H. (2002). Plant Cell. 14:1121-31.
Silva G H et al. (1999) J Mol Biol. March 5; 286(4):1123-36.
Scott L., Daniel L., C. F. Weil (1996) Genetics 142:237-246.
Scutt C P, Zubko E, Meyer P. (2002) Biochimie. 84:1119-26.
Stevens R et al. (2004). Plant Cell. January; 16(1):99-113. Epub 2003 Dec. 5.
Straub P F, Shen Q, Ho T D. (1994) Plant Mol Biol. October; 26(2):617-30.
Swoboda P, Gal S, Hohn B, Puchta H. (1994) EMBO J. 13:484-9.
Takahashi R, Joshee N, Kitagawa Y. (1994) Plant Mol Biol. October; 26(1):339-52.
Terada R et al. (2004) Plant Cell Rep. April; 22(9):653-9. Epub 2004 Jan. 23.
Vancanneyt G et al. (1990) MGG 220:245-250
Verdaguer B et al. (1996). Plant Mol Biol. 6:1129-39.
Vergunst A C et al. (2000) Chromosoma. 109:287-97.
Vilardell J et al. (1990) Plant Mol Biol. March; 14(3):423-32.
Wang et al. (1997) Nucleic Acids Res. October 1; 25(19): 3767-76.
Wang R, Zhou X, Wang X (2003) Transgenic Res. 2003 October; 12(5):529-40.
White J et al. (1990) Nucleic Acids Res. 1990 Feb. 25; 18(4): 1062.
White J (1997) Adv Pharmacol. 1997; 40:339-67
Wright D A, et al. (2005) Plant J. November; 44(4):693-705.
Xu Y et al. (1995) Plant Mol Biol March; 27(5):1060.

Yamaguchi-Shinozaki K, et al. (1993) Mol Gen Genet. January; 236(2-3):331-40.
Yoshida K, et al. (1995) Appl Microbiol Biotechnol. December; 44(3-4):466-72.
Young L W et al. (2005) Genome. June; 48(3):547-55.
Zhang W et al. (2003). Theor Appl Genet. 107:1157-68.
Zubko E, Scutt C, Meyer P. (2000) Nat Biotechnol. 2000 April; 18(4):442-5.
Zuo J, Chua N H. (2000) Curr Opin Biotechnol. April; 11(2):146-51.

The invention claimed is:

1. An isolated nucleic acid comprising a nucleic acid coding for a restriction enzyme capable of cutting a DNA sequence at a predetermined site, fused with a nucleic acid coding for a rat glucocorticoid receptor depicted in SEQ ID No. 1.

2. The isolated nucleic acid of claim 1, wherein said restriction enzyme is a meganuclease, cutting at a predetermined site of at least 15 bases.

3. The isolated nucleic acid of claim 2, wherein said meganuclease is chosen in the group consisting of I-SceI, I-CreI, I-CeuI, PI-SceI, and I-DmoI.

4. The isolated nucleic acid of claim 1, wherein said nucleic acid coding for a rat glucocorticoid receptor is fused at the 3' end of said nucleic acid coding for a restriction enzyme.

5. The isolated nucleic acid of claim 1, further comprising at least one sequence coding for a nuclear localisation signal.

6. The isolated nucleic acid of claim 1, having SEQ ID No. 8.

7. An expression cassette comprising a promoter operably linked to the isolated nucleic acid of claim 1, wherein said promoter is inducible by a steroid.

8. A transgenic plant transformed with and comprising the nucleic acid of claim 1.

9. A method for promoting a genomic double strand break at a predetermined restriction site R in the genome of an organism, comprising the steps of transforming said organism with the nucleic acid of claim 1, wherein said restriction enzyme is capable of cutting at said predetermined restriction site R, and applying dexamethasone to cells of said transformed organism in order to promote genomic double strand break at said predetermined restriction site R.

10. The method of claim 9, wherein said organism is a plant.

* * * * *

SEQUENCE LISTING

```
<160> NUMBER OF SEQ ID NOS: 13

<210> SEQ ID NO 1
<211> LENGTH: 289
<212> TYPE: PRT
<213> ORGANISM: artificial
<220> FEATURE:
<223> OTHER INFORMATION: synthetic Rat GR LBD

<400> SEQUENCE: 1

Pro Glu Ala Arg Lys Thr Lys Lys Ile Lys Gly Ile Gln Gln Ala
1               5                   10                  15

Thr Ala Gly Val Ser Gln Asp Thr Ser Glu Asn Pro Asn Lys Thr Ile
                20                  25                  30

Val Pro Ala Ala Leu Pro Gln Leu Thr Pro Thr Leu Val Ser Leu Leu
            35                  40                  45

Glu Val Ile Glu Pro Glu Val Leu Tyr Ala Gly Tyr Asp Ser Ser Val
        50                  55                  60

Pro Asp Ser Ala Trp Arg Ile Met Thr Thr Leu Asn Met Leu Gly Gly
65                  70                  75                  80

Arg Gln Val Ile Ala Ala Val Lys Trp Ala Lys Ala Ile Pro Gly Phe
                85                  90                  95

Arg Asn Leu His Leu Asp Asp Gln Met Thr Leu Leu Gln Tyr Ser Trp
            100                 105                 110

Met Phe Leu Met Ala Phe Ala Leu Gly Trp Arg Ser Tyr Arg Gln Ser
        115                 120                 125

Ser Gly Asn Leu Leu Cys Phe Ala Pro Asp Leu Ile Ile Asn Glu Gln
    130                 135                 140

Arg Met Ser Leu Pro Cys Met Tyr Asp Gln Cys Lys His Met Leu Phe
145                 150                 155                 160

Val Ser Ser Glu Leu Gln Arg Leu Gln Val Ser Tyr Glu Glu Tyr Leu
                165                 170                 175

Cys Met Lys Thr Leu Leu Leu Leu Ser Ser Val Pro Lys Glu Gly Leu
            180                 185                 190

Lys Ser Gln Glu Leu Phe Asp Glu Ile Arg Met Thr Tyr Ile Lys Glu
        195                 200                 205

Leu Gly Lys Ala Ile Val Lys Arg Glu Gly Asn Ser Ser Gln Asn Trp
    210                 215                 220

Gln Arg Phe Tyr Gln Leu Thr Lys Leu Leu Asp Ser Met His Glu Val
225                 230                 235                 240

Val Glu Asn Leu Leu Thr Tyr Cys Phe Gln Thr Phe Leu Asp Lys Thr
                245                 250                 255

Met Ser Ile Glu Phe Pro Glu Met Leu Ala Glu Ile Ile Thr Asn Gln
            260                 265                 270

Ile Pro Lys Tyr Ser Asn Gly Asn Ile Lys Lys Leu Leu Phe His Gln
        275                 280                 285

Lys

<210> SEQ ID NO 2
<211> LENGTH: 900
```

```
<212> TYPE: DNA
<213> ORGANISM: artificial
<220> FEATURE:
<223> OTHER INFORMATION: synthetic Rat GR LBD

<400> SEQUENCE: 2
ccagaagctc gaaaacaaa gaaaaaatc aaagggattc agcaagccac tgcaggagtc     60
tcacaagaca cttcggaaaa tcctaacaaa acaatagttc ctgcagcatt accacagctc   120 accccctacct tggtgtcact gctggaggtg attgaacccg aggtgttgta tgcaggatat  180
gatagctctg ttccagattc agcatggaga attatgacca cactcaacat gttaggtggg   240
cgtcaagtga ttgcagcagt gaaatgggca aaggcgatac caggcttcag aaacttacac   300
ctggatgacc aaatgacccct gctacagtac tcatggatgt ttctcatggc atttgccctg   360
ggttggagat catacagaca atcaagtgga aacctgctct gctttgctcc tgatctgatt   420
attaatgagc agagaatgtc tctaccctgc atgtatgacc aatgtaaaca catgctgttt   480
gtctcctctg aattacaaag attgcaggta tcctatgaag agtatctctg tatgaaaacc   540
ttactgcttc tctcctcagt tcctaaggaa ggtctgaaga ccaagagttt atttgatgag   600
attcgaatga cttatatcaa agagctagga aaagccatcg tcaaagggaa agggaactcc   660
agtcagaact ggcaacggtt ttaccaactg acaaagcttc tggactccat gcatgaggtg   720
gttgagaatc tccttaccta ctgcttccag acatttttgg ataagaccat gagtattgag   780
ttcccagaga tgttagctga aatcatcact aatcagatac caaatattc aaatggaaat   840 atcaaaagc ttctgtttca tcaaaaatga atcaaaagc ttctgtttca tcaaaaatga   900

<210> SEQ ID NO 3
<211> LENGTH: 10
<212> TYPE: PRT
<213> ORGANISM: artificial
<220> FEATURE:
<223> OTHER INFORMATION: synthetic SV40 NLS

<400> SEQUENCE: 3

Cys Thr Pro Pro Lys Lys Lys Arg Lys Val
1               5                   10

<210> SEQ ID NO 4
<211> LENGTH: 30
<212> TYPE: DNA
<213> ORGANISM: artificial
<220> FEATURE:
<223> OTHER INFORMATION: synthetic SV40 NLS

<400> SEQUENCE: 4
tgcaccccgc cgaagaaaaa gaggaaagtg                                      30

<210> SEQ ID NO 5
<211> LENGTH: 236
<212> TYPE: PRT
<213> ORGANISM: artificial
<220> FEATURE:
<223> OTHER INFORMATION: synthetic I-SceI

<400> SEQUENCE: 5

Met Ala Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
                20                  25                  30

Glu Gln Phe Glu Ala Gly Ile Gly Leu Ile Leu Gly Asp Ala Tyr Ile
            35                  40                  45
```

```
Arg Ser Arg Asp Glu Gly Lys Thr Tyr Cys Met Gln Phe Glu Trp Lys
     50                  55                  60

Asn Lys Ala Tyr Met Asp His Val Cys Leu Leu Tyr Asp Gln Trp Val
 65                  70                  75                  80

Leu Ser Pro Pro His Lys Lys Glu Arg Val Asn His Leu Gly Asn Leu
             85                  90                  95

Val Ile Thr Trp Gly Ala Gln Thr Phe Lys His Gln Ala Phe Asn Lys
            100                 105                 110

Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn Thr Ile Ser Ser Glu Thr Phe Leu Lys
225                 230                 235

<210> SEQ ID NO 6
<211> LENGTH: 708
<212> TYPE: DNA
<213> ORGANISM: artificial
<220> FEATURE:
<223> OTHER INFORMATION: synthetic I-SCeI

<400> SEQUENCE: 6
atggccaaaa acatcaaaaa aaaccaggta atgaacctgg gtccgaactc taaactgctg      60
aaagaataca atcccagct gatcgaactg aacatcgaac agttcgaagc aggtatcggt     120
ctgatcctgg gtgatgctta catccgttct cgtgatgaag gtaaaaccta ctgtatgcag     180
ttcgagtgga aaaacaaagc atacatggac cacgtatgtc tgctgtacga tcagtgggta     240
ctgtccccgc cgcacaaaaa agaacgtgtt aaccacctgg gtaacctggt aatcacctgg     300
ggcgcccaga ctttcaaaca ccaagctttc aacaaactgg ctaacctgtt catcgttaac     360
aacaaaaaaa ccatcccgaa caacctggtt gaaaactacc tgaccccgat gtctctggca     420
tactggttca tggatgatgg tggtaaatgg gattacaaca aaaactctac caacaaatcg     480
atcgtactga acacccagtc tttcactttc gaagaagtag aatacctggt taagggtctg     540
cgtaacaaat tccaactgaa ctgttacgta aaaatcaaca aaaacaaacc gatcatctac     600
atcgattcta tgtcttacct gatcttctac aacctgatca accgtacct gatcccgcag      660 atgatgtaca aactgccgaa cactatctcc tccgaaactt tcctgaaa                  708

<210> SEQ ID NO 7
<211> LENGTH: 539
<212> TYPE: PRT
<213> ORGANISM: artificial
<220> FEATURE:
<223> OTHER INFORMATION: synthetic fusion protein NLS-I-SceI-GR-LBD

<400> SEQUENCE: 7
```

```
Met Ala Cys Thr Pro Lys Lys Lys Arg Lys Val Leu Ala Lys Asn
1               5                   10                  15

Ile Lys Lys Asn Gln Val Met Asn Leu Gly Pro Asn Ser Lys Leu Leu
            20                  25                  30

Lys Glu Tyr Lys Ser Gln Leu Ile Glu Leu Asn Ile Gln Phe Glu
            35                  40                  45

Ala Gly Ile Gly Leu Ile Leu Gly Asp Ala Tyr Ile Arg Ser Arg Asp
50                  55                  60

Glu Gly Lys Thr Tyr Cys Met Gln Phe Glu Trp Lys Asn Lys Ala Tyr
65                  70                  75                  80

Met Asp His Val Cys Leu Leu Tyr Asp Gln Trp Val Leu Ser Pro Pro
                85                  90                  95

His Lys Lys Glu Arg Val Asn His Leu Gly Asn Leu Val Ile Thr Trp
            100                 105                 110

Gly Ala Gln Thr Phe Lys His Gln Ala Phe Asn Lys Leu Ala Asn Leu
            115                 120                 125

Phe Ile Val Asn Asn Lys Lys Thr Ile Pro Asn Asn Leu Val Glu Asn
            130                 135                 140

Tyr Leu Thr Pro Met Ser Leu Ala Tyr Trp Phe Met Asp Asp Gly Gly
145                 150                 155                 160

Lys Trp Asp Tyr Asn Lys Asn Ser Thr Asn Lys Ser Ile Val Leu Asn
                165                 170                 175

Thr Gln Ser Phe Thr Phe Glu Glu Val Glu Tyr Leu Val Lys Gly Leu
            180                 185                 190

Arg Asn Lys Phe Gln Leu Asn Cys Tyr Val Lys Ile Asn Lys Asn Lys
            195                 200                 205

Pro Ile Ile Tyr Ile Asp Ser Met Ser Tyr Leu Ile Phe Tyr Asn Leu
            210                 215                 220

Ile Lys Pro Tyr Leu Ile Pro Gln Met Met Tyr Lys Leu Pro Asn Thr
225                 230                 235                 240

Ile Ser Ser Glu Thr Phe Leu Lys Glu Leu Pro Glu Ala Arg Lys Thr
                245                 250                 255

Lys Lys Lys Ile Lys Gly Ile Gln Gln Ala Thr Ala Gly Val Ser Gln
            260                 265                 270

Asp Thr Ser Glu Asn Pro Asn Lys Thr Ile Val Pro Ala Ala Leu Pro
            275                 280                 285

Gln Leu Thr Pro Thr Leu Val Ser Leu Leu Glu Val Ile Glu Pro Glu
            290                 295                 300

Val Leu Tyr Ala Gly Tyr Asp Ser Ser Val Pro Asp Ser Ala Trp Arg
305                 310                 315                 320

Ile Met Thr Thr Leu Asn Met Leu Gly Gly Arg Gln Val Ile Ala Ala
                325                 330                 335

Val Lys Trp Ala Lys Ala Ile Pro Gly Phe Arg Asn Leu His Leu Asp
            340                 345                 350

Asp Gln Met Thr Leu Leu Gln Tyr Ser Trp Met Phe Leu Met Ala Phe
            355                 360                 365

Ala Leu Gly Trp Arg Ser Tyr Arg Gln Ser Ser Gly Asn Leu Leu Cys
            370                 375                 380

Phe Ala Pro Asp Leu Ile Ile Asn Glu Gln Arg Met Ser Leu Pro Cys
385                 390                 395                 400

Met Tyr Asp Gln Cys Lys His Met Leu Phe Val Ser Ser Glu Leu Gln
                405                 410                 415

Arg Leu Gln Val Ser Tyr Glu Glu Tyr Leu Cys Met Lys Thr Leu Leu
```

```
                       420               425               430
Leu Leu Ser Ser Val Pro Lys Glu Gly Leu Lys Ser Gln Glu Leu Phe
            435                 440                 445

Asp Glu Ile Arg Met Thr Tyr Ile Lys Glu Leu Gly Lys Ala Ile Val
        450                 455                 460

Lys Arg Glu Gly Asn Ser Ser Gln Asn Trp Gln Arg Phe Tyr Gln Leu
465                 470                 475                 480

Thr Lys Leu Leu Asp Ser Met His Glu Val Val Glu Asn Leu Leu Thr
                485                 490                 495

Tyr Cys Phe Gln Thr Phe Leu Asp Lys Thr Met Ser Ile Glu Phe Pro
            500                 505                 510

Glu Met Leu Ala Glu Ile Ile Thr Asn Gln Ile Pro Lys Tyr Ser Asn
        515                 520                 525

Gly Asn Ile Lys Lys Leu Leu Phe His Gln Lys
    530                 535

<210> SEQ ID NO 8
<211> LENGTH: 1617
<212> TYPE: DNA
<213> ORGANISM: artificial
<220> FEATURE:
<223> OTHER INFORMATION: synthetic fusion protein NLS-I-SceI-GR-LBD
<220> FEATURE:
<221> NAME/KEY: I-SceI
<222> LOCATION: (1)..(706)
<220> FEATURE:
<221> NAME/KEY: Rat_GR
<222> LOCATION: (715)..(1584)

<400> SEQUENCE: 8
atggcctgca ccccgccgaa gaaaaagagg aaagtgctgg ccaaaaacat caaaaaaaac      60
caggtaatga acctgggtcc gaactctaaa ctgctgaaag aatacaaatc ccagctgatc     120
gaactgaaca tcgaacagtt cgaagcaggt atcggtctga tcctgggtga tgcttacatc     180
cgttctcgtg atgaaggtaa aacctactgt atgcagttcg agtggaaaaa caaagcatac     240
atggaccacg tatgtctgct gtacgatcag tgggtactgt ccccgccgca aaaaaagaa     300 cgtgttaacc cctgggtaa cctggtaatc acctggggcg cccagacttt caaacaccaa     360
gctttcaaca aactggctaa cctgttcatc gttaacaaca aaaaaaccat cccgaacaac     420
ctggttgaaa actacctgac cccgatgtct ctggcatact ggttcatgga tgatggtggt     480
aaatgggatt acaacaaaaa ctctaccaac aaatcgatcg tactgaacac ccagtctttc     540
actttcgaag aagtagaata cctggttaag ggtctgcgta caaattcca actgaactgt     600 tacgtaaaaa tcaacaaaaa caaaccgatc atctacatcg attctatgtc ttacctgatc     660
ttctacaacc tgatcaaacc gtacctgatc ccgcagatga tgtacaaact gccgaacact     720
atctcctccg aaactttcct gaaagagctc ccagaagctc gaaaaacaaa gaaaaaaatc     780
aaagggattc agcaagccac tgcaggagtc tcaagacga cttcggaaaa tcctaacaaa     840
acaatagttc ctgcagcatt accacagctc accctacct ggtgtcact gctggaggtg     900 attgaacccg aggtgttgta tgcaggatat gatagctctg ttccagattc agcatggaga     960
attatgacca cactcaacat gttaggtggg cgtcaagtga ttgcagcagt gaaatgggca    1020
aaggcgatac aggcttcag aaacttacac ctggatgacc aaatgacccct gctacagtac    1080 tcatggatgt ttctcatggc atttgccctg ggttggagat catacagaca atcaagtgga    1140
aacctgctct gctttgctcc tgatctgatt attaatgagc agagaatgtc tctaccctgc    1200
atgtatgacc aatgtaaaca catgctgttt gtctcctctg aattacaaag attgcaggta    1260
```

```
tcctatgaag agtatctctg tatgaaaacc ttactgcttc tctcctcagt tcctaaggaa    1320
ggtctgaaga gccaagagtt atttgatgag attcgaatga cttatatcaa agagctagga    1380
aaagccatcg tcaaaaggga agggaactcc agtcagaact ggcaacggtt ttaccaactg    1440
acaaagcttc tggactccat gcatgaggtg gttgagaatc tccttaccta ctgcttccag    1500
acatttttgg ataagaccat gagtattgag ttcccagaga tgttagctga aatcatcact    1560
aatcagatac caaaatattc aaatggaaat atcaaaaagc ttctgtttca tcaaaaa      1617
```

<210> SEQ ID NO 9
<211> LENGTH: 68
<212> TYPE: DNA
<213> ORGANISM: artificial
<220> FEATURE:
<223> OTHER INFORMATION: synthetic primer

<400> SEQUENCE: 9

```
catggatcca ccatggcctg cacccgccg aagaaaaga ggaaagtgct ggccaaaaac      60
atcaaaaa                                                             68
```

<210> SEQ ID NO 10
<211> LENGTH: 26
<212> TYPE: DNA
<213> ORGANISM: artificial
<220> FEATURE:
<223> OTHER INFORMATION: synthetic primer

<400> SEQUENCE: 10

```
cgcgagctct ttcaggaaag tttcgg                                         26
```

<210> SEQ ID NO 11
<211> LENGTH: 24
<212> TYPE: DNA
<213> ORGANISM: artificial
<220> FEATURE:
<223> OTHER INFORMATION: synthetic primer

<400> SEQUENCE: 11

```
aattctaggg ataacagggt aata                                           24
```

<210> SEQ ID NO 12
<211> LENGTH: 24
<212> TYPE: DNA
<213> ORGANISM: artificial
<220> FEATURE:
<223> OTHER INFORMATION: synthetic primer

<400> SEQUENCE: 12

```
agcttattac cctgttatcc ctag                                           24
```

<210> SEQ ID NO 13
<211> LENGTH: 1309
<212> TYPE: DNA
<213> ORGANISM: artificial
<220> FEATURE:
<223> OTHER INFORMATION: synthetic Lim10 promoter

<400> SEQUENCE: 13

```
tgcacatgta agtcctgcgt actcatataa aaaagtgaac atacacacga gtatggtttg     60
cttccaccta gtcatcgtat attccagatt tgtcaaacac gatatatttg catacatatc    120
ctccgaatgt ttgtgcatat caaaaagtac atgtgtacca ctaacaacta tgtgcacata    180
ataatgtcaa ccttcacttc aacttacaac ccatgtatgc atactttttt tatccactac    240
```

```
-continued atggacctat atatatagaa atttgaacta aatatccagc ttcattaata ttgttagctt    300
aacatgcatc tctacttcat tatgcatctt gatgttccca ttgatgaaat cttcctcact    360
aataatcatc acacatctag cctcttcacc agagagcatc acacatcaac agtcttcaaa    420
attcagtgtc caacaacacg gatcttattg tgcatcagtt aacaccctgc gtacccactt    480
caccaaagat cataacacat tattggcctt caaaattcaa tgcccaacaa cacgaatcat    540
gtcgtacatc aatcatgtcg tacatcagtt atcaccccgc gttctagctg catcttccaa    600
aggctgctta cgcaccccgc aatggtagaa tgatcaagct ggttgttcct ataagtgagt    660
agagaaacac atgaatcagg ctccacaaac acatactgta tttcttttct taacgtcatt    720
tttaacaaat tataatatta aaatttctct aaggtcagag attaccacac ataaaaaagt    780
aaattttagt atctttaaac tcatataaaa tagaatggac aaaatattat aaatcataag    840
acaaccaacc aattccacat tatactaaat gaaatatcac aaatatgaca aataattaaa    900
aaaaaaaatc gcatggtttt cagaaattgg aggggtaaga taagaaataa gtcatcctca    960
aaatacgcgg cggggcacgt gtgaattcat tttgtcggta gaaacacagc tcgttttta    1020 ctatgacgat accaacctta cgtaatacat tcgttccatc aacatgatcg gaattgacac    1080
agaaaacctc ggttcaaatt tcaccggttt caatctcgac cgctagccgg ccgaaggcag    1140
acctctgcca cccatgaaag cacgagaagc ttccatcctc ttcttgaccc tttgtgaagc    1200
atcgagacct cttccctcag tctttatata aaccccaac ccactcccaa ttccaccgtc    1260
tccatcgaac accagataag tggacctcaa agaaatcaag atccatgca                1309
```